(12) United States Patent
Bradley et al.

(10) Patent No.: US 7,309,712 B2
(45) Date of Patent: Dec. 18, 2007

(54) 1H-PYRAZOLES USEFUL IN THERAPY

(75) Inventors: Paul Anthony Bradley, Sandwich (GB); Kevin Neil Dack, Sandwich (GB); Patrick Stephen Johnson, Sandwich (GB); Sarah Elizabeth Skerratt, Sandwich (GB)

(73) Assignee: Pfizer Limited, Sandwich (GB)

( * ) Notice: Subject to any disclaimer, the term of this patent is extended or adjusted under 35 U.S.C. 154(b) by 0 days.

(21) Appl. No.: 11/592,574

(22) Filed: Nov. 3, 2006

(65) Prior Publication Data

US 2007/0105909 A1  May 10, 2007

Related U.S. Application Data

(60) Provisional application No. 60/735,091, filed on Nov. 8, 2005.

(51) Int. Cl.
  *A61K 31/44* (2006.01)
  *C07D 401/00* (2006.01)
  *C07D 231/10* (2006.01)

(52) U.S. Cl. .................. 514/341; 514/408; 548/275.4; 548/376.1

(58) Field of Classification Search ............. 546/275.4; 514/341, 406; 548/376.1
See application file for complete search history.

(56) References Cited

U.S. PATENT DOCUMENTS

| 4,737,451 A * | 4/1988 | Ichijima ..................... 430/544 |
| 5,510,365 A * | 4/1996 | Wachtler et al. ............. 514/407 |
| 2003/0100554 A1 | 5/2003 | Jones et al. ............... 514/230.5 |

FOREIGN PATENT DOCUMENTS

WO  WO 2004/056782  7/2004

OTHER PUBLICATIONS

Endometriosis from national institutes of Health, retrieved on May 31, 2007 from <http://www.nichd.nih.gov/publications/pubs/uplaod/endometriosis-2002.pdf>.*
Adenomyosis from Medline Plus Medical Encyclopedia, retrieved on May 31, 2007 from <http://www.nlm.nih.gov/medlineplus/ency/article/001513.htm>.*
Kettel et al., A. J. Obs. Gyn., vol. 178 (6), 1151-1156, 1998.*
Chwalisz et al., Fetility & Sterility, 82(2), S83-S84, 2004.*
K. Chwalisz et al., Fertility & Sterility, vol. 82, Suppl. 2, pp. S83-S84, (Abstract 0-207), Sep. 2004.
L. Michael Kettel et al., American Journal of Obstetric & Gynecology, vol. 178, No. 6, pp. 1151-1156, Jun. 1998.
H. Nagasawa, et al., Anticancer Research, vol. 9, pp. 827-832, 1989.
Y.-F. Zhou et al., Life Sciences, vol. 67, pp. 2713-2720, 2000.
Y.-F. Zhou et al., Fertility and Sterility, vol. 80, Suppl. 2, pp. 788-794, 2003.

* cited by examiner

*Primary Examiner*—Rebecca Anderson
*Assistant Examiner*—Susannah Chung
(74) *Attorney, Agent, or Firm*—Gregg C. Benson; Carl J. Goddard

(57) ABSTRACT

Compounds of formula (I),

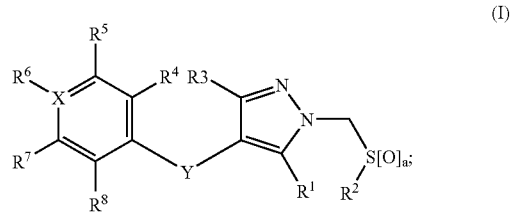

or a pharmaceutically acceptable derivative thereof, wherein $R^1$ and $R^3$ independently represent H, $C_{1-6}$alkyl, $C_{3-8}$cycloalkyl, or halogen; $R^2$ represents $C_{1-6}$alkyl, $CF_3$ or aryl; a represents 1 or 2; $R^4$, $R^5$, $R^7$ and $R^8$ independently represent H, $C_{1-6}$alkyl, $C_{1-6}$alkyloxy, CN or halogen, or $R^4$ and $R^5$, or $R^7$ and $R^8$, together with the ring to which they are attached form an aryl or heterocyclic fused ring system; X represents C or N; Y represents $CH_2$ or O; $R^6$ represents H, CN or halo provided that, when X represents N, $R^6$ is absent. The compounds are useful for treating endometriosis, uterine fibroids (leiomyomata), menorrhagia, adenomyosis, primary and secondary dysmenorrhoea (including symptoms of dyspareunia, dyschexia and chronic pelvic pain), or chronic pelvic pain syndrome.

18 Claims, No Drawings

1H-PYRAZOLES USEFUL IN THERAPY

This application claims priority to U.S. Provisional Application Ser. No. 60/735,091, filed Nov. 8, 2005.

BACKGROUND OF THE INVENTION

This invention relates to novel compounds, and their derivatives, which are useful in therapy and to processes for their preparation. It also relates to intermediates used in the preparation of such compounds and derivatives, compositions containing them and their uses.

Endometriosis is a common gynaecological disease that affects 10-20% women of reproductive age and manifests itself in the presence of functional ectopic endometrial glands and stroma at locations outside the uterine cavity {Prentice, (2001), BMJ, 323, 93-95}. Patients with endometriosis may present with many different symptoms and severity. Most commonly this is dysmenorrhoea, but chronic pelvic pain, dyspareunia, dyschexia, menorrhagia, lower abdominal or back pain, infertility, bloating and pain on micturition are also part of the constellation of symptoms of endometriosis.

Originally described by Von Rokitansky {Von Rokitansky, (1860), Ztsch. K K Gesellsch. der Aerzte zu Wien, 37, 577-581}, the exact pathogenesis of endometriosis is unclear {Witz, (1999), Clin. Obstet. Gynaecol., 42, 566-585.; Witz, (2002), Gynaecol. & Obstet. Invest., 53, 52-62.}, but the most widely accepted theory is the implantation, or Sampson Theory {Sampson, (1927), Am. J. Obstet. Gynaecol., 14, 422-429.}. The Sampson Theory proposes that the development of endometriosis is a consequence of retrograde dissemination and implantation of endometrial tissue into the peritoneal cavity during menstruation. Following attachment, the fragments of endometrium recruit vascular supply and undergo cycles of proliferation and shedding under local and systemic hormonal controls. In women with patent fallopian tubes, retrograde menstruation appears to be universal (Liu, Brit. J. Obstet. Gynaecol., 93, 859-862). The disease often manifests itself as rectovaginal endometriosis or adenomyosis, ovarian cystic endometriomas and, most commonly, peritoneal endometriosis. The major sites of attachment and lesion growth within the pelvis are the ovaries, broad and round ligaments, fallopian tubes, cervix, vagina, peritoneum and the pouch of Douglas. At its most severe, endometriosis can cause profound structural modification to peritoneal cavity, including multi-organ adhesions and fibrosis.

Symptomatic endometriosis can be managed medically and surgically, where the intention is to remove the ectopic lesion tissue. Surgical intervention can be either conservative, aiming to preserve the reproductive potential of the patient, or comparatively radical for severe disease, involving dissection of the urinary tract, bowel, and rectovaginal septum, or total abdominal hysterectomy and bilateral salpingo-oopherectomy. Medical pharmacological treatments such as the androgenic therapies, danazol and gestrinone, the constellation of GnRH agonists, buserelin, goserelin, leuprolide, nafarelin and triptorelin, GnRH antagonists, cetrorelix and abarelix, as well as the progestogens, including medroxyprogesterone acetate, induce lesion atrophy by suppressing the production of estrogen. These approaches are not without unwanted side effects; danazol and gestrinone include weight gain, hirsuitism, acne, mood changes and metabolic effects on the cardiovascular system. The group of GnRH agonists and antagonists are found to cause a profound suppression of estrogen leading to vasomotor effects (hot flashes) and depletion of bone mineral density, which restricts their use to only six months of therapy. The group of progestogens, including medroxyprogesterone acetate, suppress the gonadotropins, but do not down-regulate ovarian estrogen production to the same extent as the GnRH analogues. The side effects include irregular bleeding, bloating, weight gain and metabolic effects on the cardiovascular system.

Uterine leiomyomas {Flake, et al. (2003), Environ. Health Perspect., 111, 1037-1054.; Walker, (2002), Recent Prog. Hormone Res., 57, 277-294.}, or fibroids, are the most common benign tumours found in women and occur in the majority of women by the time they reach the menopause. Although uterine fibroids are the most frequent indication for hysterectomy in the United States, as with endometriosis, remarkably little is known about the underlying pathophysiology of the disease. As with endometriotic lesions, the presence of enlarged uterine fibroids is associated with abnormal uterine bleeding, dysmenorrhoea, pelvic pain and infertility. Outside of surgical management, medical treatments commonly used for endometriosis, such as GnRH analogues or danazol, have been shown to suppress fibroid growth by inducing a reversible hypoestrogenic state {Chrisp, (1990), Drugs 39, 523-551.; Chrisp, (1991), Drugs, 41, 254-288.; De Leo, et al. (2002), Drug Safety 25, 759-779.; Ishihara, et al. (2003) Fertility & Sterility 79, 735-742}. However, the future disease management of both uterine fibroids and endometriosis will rely on the development of more effective, well-tolerated and safer agents than those that are currently available.

Steroidal progestins (i.e., progesterone receptor agonists) are commonly used in women's health, such as in contraception and hormone therapy and for the treatment of gynecological disorders. Recent studies in women and in nonhuman primates also indicate that progesterone receptor antagonists may have potential applications in contraception and for the treatment of reproductive disorders such as fibroids and endometriosis. Currently, all clinically available progesterone receptor agonists and antagonists are steroidal compounds. They often cause various side effects due to their functional interactions with other steroid receptors or because of effects associated with their steroidal metabolites {Winneker, et al.; Sem. Repro. Med. (2005), 23(1), 46-57}.

Progesterone receptor antagonists [anti-progestins (APs)], including the founding members of the class mifepristone (RU-486; Roussel UCLAF), onapristone (ZK 98 299); Schering AG), ZK 137 316 and ZK-230 211, are compounds that bind to the progesterone receptor (PR) and prevent progesterone-induced gene expression {(Spitz, (2003), Steroids, 68, 981-993.)}. Acting on the estrogen primed endometrium, progesterone plays an essential role in the differentiation and ductal morphogenesis of endometrial tissue, but also participates in the inhibition of myometrial contractility and the polarisation of leukocyte Th1/Th2 responses that are critical for embryo implantation and the maintenance of pregnancy. A number of studies have investigated the potential beneficial effects of anti-progestins on the signs and symptoms of endometriosis {Grow, et al. (1996), J. Clin. Endocrin. Metabol., 81, 1933-1939.; Kettel, et al. (1996). Fertility & Sterility, 65, 23-28.; Kettel, et al. (1998), Am. J. Obstet. Gynaecol., 178, 1151-1156.} and uterine fibroids {Eisinger, et al. (2003), Obstet. Gynaecol., 101, 243-250.; Murphy, et al. (1994), Curr. Op. Obstet. Gynaecol., 6, 269-278.; Murphy, et al. (1995), Fertility & Sterility, 63, 761-766.; Steinauer, et al. (2004), Obst. Gynaecol., 103, 1331-1336.; Yang, et al. (1996), Chinese. Chung-Hua Fu Chan Ko Tsa Chih [Chinese Journal of Obstet.

Gynaecol.], 31, 624-626.}. Unlike GnRH analogues, and other conventional pharmacological approaches, anti-progestins, especially mifepristone, appear to be able to reduce lesion or fibroid volume, whilst maintaining a tonic level of ovarian oestrogen secretion. Such anti-progestins induce amenorrhoea and endometrial compaction, and also appear to sufficiently protect against rapid oestrogen-dependent bone loss {Grow, et al. (1996), J. Clin. Endocrin. & Metabol., 81, 1933-1939.}. In contrast GnRH analogues cause a rapid loss in bone mineral density, a clinical feature which limits their treatment duration to 6 months. Whilst mifepristone is a potent anti-progestin, it also has equipotent anti-glucocorticoid activity. Outside of a palliative treatment of hypercortisolism for Cushing's Syndrome {Chu, et al. (2001), J. Clin. Endocrin. Metabol., 86, 3568-3573.; Sartor, (1996), Clin. Obstet. Gynaecol., 39, 506-510.; Spitz, (2003), Steroids, 68, 981-993.; Van Look, (1995), Human Reproduction Update, 1, 19-34.}, the anti-glucocorticoid activity is an undesirable feature of mifepristone and potentially many of the steroidal classes of anti-progestins.

A further class of steroidal and non-steroidal compounds, termed the progesterone receptor modulators (PRMs, or mesoprogestins), including asoprisnil (J867, benzaldehyde, 4-[(11β, 17β)-17-methoxy-17-(methoxymethyl)-3-oxoestra-4,9-dien-11-yl]-, 1-oxime; Jenpharm, TAP), J912, J956, J1042, have also been described. In addition to their potential utility in hormone replacement and as contraceptives, these classes of compounds could be considered to have utility in the treatment of endometriosis and uterine leiomyoma {Chwalisz, et al. (2004), Semin. Reprod. Med., 22, 113-119.; Chwalisz, et al. (2002), Ann. N.Y. Acad. Sci., 955, 373-388; discussion 389-393.; DeManno, et al. (2003), Steroids, 68, 1019-1032.}. Asoprisnil and structurally-related PRMs differ from anti-progestins and progestins in animal models, demonstrating partial progestogenic activity in the rabbit endometrium McPhail's Test {McPhail, (1934), J. Physiol., 83, 145-156.}) and guinea pig vagina, for instance. Pre-clinical studies with asoprisinil in primates have indicated that PRMs suppress endometrial growth and, unlike the effects of progestins, endometrial ER and PR expression is not repressed {Chwalisz, et al. (2000), Steroids, 65, 741-751.; DeManno, et al. (2003), Steroids, 68, 1019-1032.; Elger, et al. (2000), Steroids 65, 713-723.}.

The compounds of the present invention have been found to have useful pharmaceutical properties. They may be used to treat endometriosis, uterine fibroids (leiomyomata) and menorrhagia, adenomyosis, primary and secondary dysmenorrhoea (including symptoms of dyspareunia, dyschexia and chronic pelvic pain), chronic pelvic pain syndrome, precocious puberty, cervical ripening, contraception (emergency), breast carcinoma, ovarian carcinoma, endometrial carcinoma, prostate carcinoma, pulmonary carcinoma, testicular carcinoma, gastric carcinoma, meningioma, anxiety, premenstrual syndrome, premenstrual dysphoric disorder, alcohol abuse and reward, or Charcot-Marie-Tooth disease.

Particularly of interest are the following diseases or disorders: endometriosis, uterine fibroids (leiomyomata), menorrhagia, adenomyosis, primary and secondary dysmenorrhoea (including symptoms of dyspareunia, dyschexia and chronic pelvic pain), and chronic pelvic pain syndrome.

In particular, the compounds and derivatives of the present invention exhibit activity as progesterone receptor antagonists and may be useful for treatment where progesterone receptor antagonism is indicated. More particularly, the compounds and derivatives of the present invention may be useful for treating endometriosis and/or uterine fibroids (leiomyomata).

International Patent Application WO 02/085860 describes pyrazole derivatives of the formula

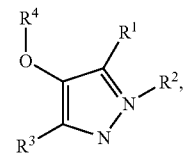

wherein $R^1$, $R^2$, $R^3$ and $R^4$ are as defined therein, which are modulators of HIV reverse transcriptase.

According to the present invention, there is provided a compound of the formula (I)

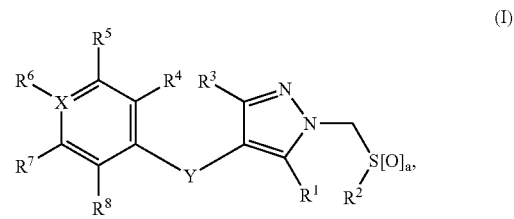

(I)

or a pharmaceutically acceptable derivative thereof, wherein:

$R^1$ and $R^3$ independently represent H, $C_{1-6}$-alkyl, $C_{3-8}$cycloalkyl, or halogen;

$R^2$ represents $C_{1-6}$-alkyl, $CF_3$ or aryl;

a represents 1 or 2;

$R^4$, $R^5$, $R^7$ and $R^8$ independently represent H, $C_{1-6}$alkyl, $C_{1-6}$alkyloxy, CN or halogen, or $R^4$ and $R^5$, or $R^7$ and $R^8$, together with the ring to which they are attached form an aryl or heterocyclic fused ring system;

X represents C or N;

Y represents $CH_2$ or O; and $R^6$ represents H, CN or halo provided that, when X represents N, $R^6$ is absent.

In the above definitions alkyl groups containing the requisite number of carbon atoms, except where indicated, can be unbranched or branched chain. Examples include methyl, ethyl, n-propyl, i-propyl, n-butyl, i-butyl, sec-butyl and tert-butyl. Examples of alkyloxy include methoxy, ethoxy, n-propyloxy, i-propyloxy, n-butyloxy, i-butyloxy, sec-butyloxy and tert-butyloxy. Examples of cycloalkyl include cyclopropyl, cyclobutyl, cyclopentyl, cyclohexyl and cycloheptyl. The term halogen means fluoro, chloro, bromo or iodo.

Aryl rings included within the definition of aryl are phenyl or napthyl.

Heterocycles included within the definition of heterocyclic ring are pyrrolyl, imidazolyl, triazolyl, thienyl, furyl, thiazolyl, oxazolyl, thiadiazolyl, oxadiazolyl, pyridinyl, pyrimidinyl, pyridazinyl, pyrazinyl, indolyl, isoindolyl, quinolinyl, isoquinolinyl, benzimidazolyl, quinazolinyl, phthalazinyl, benzoxazolyl and quinoxalinyl, together with partially or fully saturated versions thereof as well as azetidinyl, pyrrolidinyl, piperidinyl, piperazinyl, homopiperazinyl, oxazepanyl, and morpholinyl.

In an embodiment of the invention $R^1$ represents $C_{1-6}$alkyl or $C_{3-8}$cycloalkyl.

In a further embodiment of the invention $R^2$ represents $C_{1-6}$alkyl.

In a still further embodiment of the invention $R^3$ represents $C_{1-6}$alkyl or $C_{3-8}$cycloalkyl.

In a further embodiment of the invention $R^4$ represents H.

In a still further embodiment of the invention $R^5$ represents H, $C_{1-6}$alkyl, or halogen.

In a further embodiment of the invention $R^4$ and $R^5$ together represent a phenyl or pyridinyl ring fused to the ring to which they are attached. Preferably $R^4$ and $R^5$ together represent a phenyl ring fused to the ring to which they are attached.

In a still further embodiment of the invention $R^6$ represents CN.

In a further embodiment of the invention $R^7$ represents H, $C_{1-6}$alkyl, or halogen.

In a still further embodiment of the invention $R^8$ represents H.

In a further embodiment of the invention $R^7$ and $R^8$ together represent a phenyl or pyridinyl ring fused to the ring to which they are attached. Preferably $R^7$ and $R^8$ together represent a phenyl ring fused to the ring to which they are attached.

In a still further embodiment of the invention Y represents O.

In a further embodiment of the invention halogen represents fluoro or chloro.

Preferred compounds according to the present invention are:
4-(3,5-dicyclopropyl-1-methanesulfonylmethyl-1H-pyrazol-4-yloxy)-benzonitrile;
4-(3,5-dicyclopropyl-1-methanesulfonylmethyl-1H-pyrazol-4-yloxy)-2-methyl-benzonitrile;
4-(3,5-dicyclopropyl-1-methanesulfonylmethyl-1H-pyrazol-4-yloxy)-2,6-dimethyl-benzonitrile;
2-chloro-4-(3,5-dicyclopropyl-1-methanesulfonylmethyl-1H-pyrazol-4-yloxy)-benzonitrile;
4-(3,5-dicyclopropyl-1-methanesulfonylmethyl-1H-pyrazol-4-yloxy)-2-fluoro-benzonitrile;
3-chloro-4-(3,5-dicyclopropyl-1-methanesulfonylmethyl-1H-pyrazol-4-yloxy)-benzonitrile;
4-(3,5-dicyclopropyl-1-methanesulfonylmethyl-1H-pyrazol-4-yloxy)-3-fluoro-benzonitrile;
4-(3,5-dicyclopropyl-1-methanesulfonylmethyl-1H-pyrazol-4-yloxy)-3-methoxy-benzonitrile;
4-(3,5-dicyclopropyl-1-methanesulfonylmethyl-1H-pyrazol-4-yloxy)-naphthalene-1-carbonitrile;
5-(3,5-dicyclopropyl-1-methanesulfonylmethyl-1H-pyrazol-4-yloxy)-quinoline-8-carbonitrile;
4-(3,5-dicyclopropyl-1-methanesulfonylmethyl-1H-pyrazol-4-yloxy)-quinoline;
4-(4-chloro-3-fluoro-phenoxy)-3,5-dicyclopropyl-1-methanesulfonylmethyl-1H-pyrazole;
3,5-dicyclopropyl-4-(3,4-difluoro-phenoxy)-1-methanesulfonylmethyl-1H-pyrazole;
3,5-dicyclopropyl-1-methanesulfonylmethyl-4-(3,4,5-trifluoro-phenoxy)-1H-pyrazole;
3,5-dicyclopropyl-4-(3,5-difluoro-phenoxy)-1-methanesulfonylmethyl-1H-pyrazole;
3,5-dicyclopropyl-1-methanesulfonylmethyl-4-(2,4,5-trifluoro-phenoxy)-1H-pyrazole;
4-(3-cyclopropyl-1-methanesulfonylmethyl-5-methyl-1H-pyrazol-4-yloxy)-2-methyl-benzonitrile;
4-(5-cyclopropyl-1-methanesulfonylmethyl-3-methyl-1H-pyrazol-4-yloxy)-2-methyl-benzonitrile;
4-(3-cyclopropyl-1-methanesulfonylmethyl-5-methyl-1H-pyrazol-4-yloxy)-2,6-dimethyl-benzonitrile;
4-(5-cyclopropyl-1-methanesulfonylmethyl-3-methyl-1H-pyrazol-4-yloxy)-2,6-dimethyl-benzonitrile;
4-(1-methanesulfonylmethyl-3,5-dimethyl-1H-pyrazol-4-yloxy)-2,6-dimethyl-benzonitrile;
4-(3,5-diethyl-1-methanesulfonylmethyl-1H-pyrazol-4-yloxy)-benzonitrile;
4-(3,5-diethyl-1-methanesulfonylmethyl-1H-pyrazol-4-yloxy)-2,6-dimethyl-benzonitrile;
4-(3,5-di-tert-butyl-1-methanesulfonylmethyl-1H-pyrazol-4-yloxy)-benzonitrile;
4-(3-tert-butyl-1-methanesulfonylmethyl-5-methyl-1H-pyrazol-4-yloxy)-benzonitrile;
4-(5-tert-butyl-1-methanesulfonylmethyl-3-methyl-1H-pyrazol-4-yloxy)-benzonitrile;
4-(3-chloro-5-cyclopropyl-1-methanesulfonylmethyl-1H-pyrazol-4-yloxy)-2,6-dimethyl-benzonitrile;
4-(5-chloro-3-cyclopropyl-1-methanesulfonylmethyl-1H-pyrazol-4-yloxy)-2,6-dimethyl-benzonitrile;
4-(3-cyclopropyl-1-methanesulfonylmethyl-1H-pyrazol-4-yloxy)-2,6-dimethyl-benzonitrile;
4-(5-cyclopropyl-1-methanesulfonylmethyl-1H-pyrazol-4-yloxy)-2,6-dimethyl-benzonitrile;
4-(3,5-diethyl-1-methanesulfonylmethyl-1H-pyrazol-4-ylmethyl)-benzonitrile;
4-(3,5-dicyclopropyl-1-trifluoromethanesulfonylmethyl-1H-pyrazol-4-yloxy)-benzonitrile;
4-(3,5-dicyclopropyl-1-methanesulfonylmethyl-1H-pyrazol-4-yloxy)-benzonitrile;
4-[3,5-dicyclopropyl-1-(propane-2-sulfonylmethyl)-1H-pyrazol-4-yloxy]-benzonitrile;
4-[3,5-dicyclopropyl-1-(2-methyl-propane-2-sulfonylmethyl)-1H-pyrazol-4-yloxy]-benzonitrile;
4-(1-benzenesulfonylmethyl-3,5-dicyclopropyl-1H-pyrazol-4-yloxy)-benzonitrile;
4-(3,5-diethyl-1-methanesulfinylmethyl-1H-pyrazol-4-yloxy)-2,6-dimethyl-benzonitrile;
4-(3,5-diethyl-1-methanesulfinylmethyl-1H-pyrazol-4-yloxy)-2,6-dimethyl-benzonitrile;

and the pharmaceutically acceptable derivatives thereof.

The above described embodiments of the invention may be combined with one or more further embodiments such that further embodiments are provided wherein two or more variables are defined more specifically in combination. For example, within the scope of the invention is a further embodiment wherein the variables $R^1$, $R^2$ and L all have the more limited definitions assigned to them in the more specific embodiments described above. All such combinations of the more specific embodiments described and defined above are within the scope of the invention.

Pharmaceutically acceptable derivatives of the compounds of formula (I) according to the invention include salts, solvates, complexes, polymorphs and crystal habits thereof, prodrugs, stereoisomers, geometric isomers, tautomeric forms, and isotopic variations of compounds of formula (I). Preferably, pharmaceutically acceptable derivatives of compounds of formula (I) comprise salts, solvates, esters and amides of the compounds of formula (I). More preferably, pharmaceutically acceptable derivatives of compounds of formula (I) are salts and solvates.

The pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/ chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemi-salts of acids and bases may also be formed, for example, hemi-sulphate and hemicalcium salts. See *Handbook of Pharmaceutical Salts: Properties, Selection, and Use* by Stahl and Wermuth (Wiley-VCH, 2002).

Pharmaceutically acceptable salts of compounds of formula I may be prepared by one or more of three methods:
(i) reacting the compound of formula (I) with the desired acid or base;
(ii) removing an acid- or base-labile protecting group from a suitable precursor of the compound of formula (I) or by ring-opening a suitable cyclic precursor, for example, a lactone or lactam, using the desired acid or base; or
(iii) converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterised by a change of state, typically second order (glass transition). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order (melting point).

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together {Almarsson, Chem. Comm., 17, 1889-1896, (2004)}. For a general review of multi-component complexes, see Haleblian, J. Pharm. Sci., 64 (8), 1269-1288, (1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as "lyotropic". Compounds that have the potential to form lyotropic mesophases are described as 'amphiphilic' and consist of molecules which possess an ionic (such as $-COO^-Na^+$, $-COO^-K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

As indicated above, so-called "prodrugs" of the compounds of formula (I) are also within the scope of the invention. Thus certain derivatives of compounds of formula (I), which may have little or no pharmacological activity themselves, can be converted into compounds of formula I having the desired activity, for example by hydrolytic cleavage, when administered into, or onto, the body. Such derivatives are referred to as "prodrugs". Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, Am. Pharm. Assoc.).

Prodrugs in accordance with the invention can be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include:
(i) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and (ii) where the compound of formula (I) contains a primary or secondary amino functionality (—$NH_2$ or —NHR where R≠H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Thus within the scope of the invention are envisaged the metabolites of the compounds of formula (I) when formed in vivo.

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism (tautomerism) can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or precursor) may be reacted with a suitable optically active compound, for example, an alcohol, or, in the case where the compound of formula (I) contains an acidic or basic moiety, a base or acid, such as 1-phenylethylamine or tartaric acid. The resulting diastereomeric mixture may be separated by chromatography and/or fractional crystallization and one or both of the diastereoisomers converted to the corresponding pure enantiomer(s) by conventional means.

Chiral compounds of the invention (and chiral precursors) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0% to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques, for example, *Stereochemistry of Organic Compounds* by E. L. Eliel and S. H. Wilen (Wiley, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g., $D_2O$, $d_6$-acetone, $d_6$-DMSO.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention may be administered alone or in combination with one or more other compounds of the invention or in combination with one or more other drugs, or as any combination thereof.

The compounds of the present invention may be administered in combination with COX inhibitors. Thus in a further aspect of the invention, there is provided a pharmaceutical product containing a progesterone receptor antagonist and one or more COX inhibitors as a combined preparation for simultaneous, separate or sequential use in the treatment of endometriosis. COX inhibitors useful for combining with the compounds of the present invention may include, but are not limited to:

(i) ibuprofen, naproxen, benoxaprofen, flurbiprofen, fenoprofen, fenbufen, ketoprofen, indoprofen, pirprofen, carprofen, oxaprozin, prapoprofen, miroprofen, tioxaprofen, suprofen, alminoprofen, tiaprofenic acid, fluprofen, bucloxic acid, indomethacin, sulindac, tolmetin, zomepirac, diclofenac, fenclofenec, alclofenac, ibufenac, isoxepac, furofenac, tiopinac, zidometacin, acetyl salicylic acid, indometacin, piroxicam, tenoxicam, nabumetone, ketorolac, azapropazone, mefenamic acid, tolfenamic acid, diflunisal, podophyllotoxin derivatives, acemetacin, droxicam, floctafenine, oxyphenbutazone, phenylbutazone, proglumetacin, acemetacin, fentiazac, clidanac, oxipinac, mefenamic acid, meclofenamic acid, flufenamic acid, niflumic acid, flufenisal, sudoxicam, etodolac, piprofen, salicylic acid, choline magnesium trisalicylate, salicylate, benorylate, fentiazac, clopinac, feprazone, isoxicam and 2-fluoro-α-methyl[1,1'-biphenyl]-4-acetic acid, 4-(nitrooxy)butyl ester (Wenk, et al., Eur. J. Pharmacol., 453, 319-324 (2002));

(ii) meloxicam, (U.S. Pat. No. 4,233,299), or a pharmaceutically acceptable salt or prodrug thereof;

(iii) celecoxib (U.S. Pat. No. 5,466,823), valdecoxib (U.S. Pat. No. 5,633,272), deracoxib (U.S. Pat. No. 5,521,207), rofecoxib (U.S. Pat. No. 5,474,995), etoricoxib (WO 98/03484), JTE-522 (Japanese Pat. Application Pub. No. 9052882), or a pharmaceutically acceptable salt or prodrug thereof;

(iv) parecoxib (U.S. Pat. No. 5,932,598), which is a therapeutically effective prodrug of the tricyclic COX-2 selective inhibitor valdecoxib (U.S. Pat. No. 5,633,272), in particular sodium parecoxib;

(v) ABT-963 (WO 00/24719);

(vi) nimesulide (U.S. Pat. No. 3,840,597), flosulide (J. Carter, Exp. Opin. Ther. Pat., 8(1), 21-29 (1997)), NS-398 (U.S. Pat. No. 4,885,367), SD 8381 (U.S. Pat. No. 6,034,256), BMS-347070 (U.S. Pat. No. 6,180,651), S-2474 (Eur. Pat. Pub. No. 595546) and MK-966 (U.S. Pat. No. 5,968,974);

(vii) darbufelone (Pfizer), CS-502 (Sankyo), LAS 34475 (Almirall Profesfarma), LAS 34555 (Almirall Profesfarma), S-33516 (Servier), SD 8381 (U.S. Pat. No. 6,034,256), BMS-347070 (U.S. Pat. No. 6,180,651), MK-966 (Merck), L-783003 (Merck), T-614 (Toyama), D-1367 (Chiroscience), L-748731 (Merck), CT3 (Atlantic Pharmaceutical), CGP-28238 (Novartis), BF-389 (Biofor/Scherer), GR-253035 (Glaxo Wellcome), 6-dioxo-9H-purin-8-yl-cinnamic acid (Glaxo Wellcome), and S-2474 (Shionogi).

The compounds of the present invention may be administered in combination with PDE5 inhibitors. Thus in a further aspect of the invention, there is provided a pharmaceutical product containing a progesterone receptor antagonist and one or more PDEV inhibitors as a combined preparation for simultaneous, separate or sequential use in the treatment of endometriosis. PDEV inhibitors useful for combining with compounds of the present invention include, but are not limited to:

(i) 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil, e.g., Viagra®) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP 0463756); 5-(2-ethoxy-5-morpholinoacetylphenyl)-1-methyl-3-n-propyl-1,6-dihydro-7H-pyrazolo[4,3-d]pyrimidin-7-one (see EP 0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (WO 98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (WO 99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (WO 99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (WO 01/27113, Example 8); 5-[2-iso-butoxy-5-(4-ethylpiperazin-1-ylsulphonyl)pyridin-3-yl]-3-ethyl-2-(1-methylpiperidin4-yl)-2,6-dihydro-7H-pyrazolo[4,3-d]pyrimidin-7-one (WO 01/27113, Example 15); 5-[2-ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (WO 01/27113, Example 66); 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one (WO 01/27112, Example 124); 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)pyrazino[2',1':6,1]pyrido[3,4-b]indole-1,4-dione (tadalafil, Cialis®), i.e., Examples 78 and 95 of WO 95/19978, as well as Examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil, LEVITRA®) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e., Examples 20, 19, 337 and 336 of WO99/24433; Example 11 of WO93/07124 (EISAI); compounds 3 and 14 of Rotella, J., Med. Chem., 2000, 43, 1257; 4-(4-chlorobenzyl)amino-6,7,8-trimethoxyquinazoline; N-[[3-(4,7-dihydro-1-methyl-7-oxo-3-propyl-1H-pyrazolo[4,3-d]-pyrimidin-5-yl)-4-propoxyphenyl]sulfonyl]-1-methyl-2-pyrrolidine propanamide [DA-8159, Example 68 of WO 00/27848]; and 7,8-dihydro-8-oxo-6-[2-propoxyphenyl]-1H-imidazo[4,5-g]quinazoline and 1-[3-[1-[(4-fluorophenyl) methyl]-7,8-dihydro-8-oxo-1H-imidazo[4,5-g]quinazolin-6-yl]-4-propoxyphenyl]carboxamide; 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide (TA-1790); 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzene sulfonamide (DA 8159) and pharmaceutically acceptable salts thereof; 4-bromo-5-(pyridylmethylamino)-6-[3-(4-chlorophenyl)-propoxy]-3(2H)pyridazinone; 1-[4-[(1,3-benzodioxol-5-ylmethyl)amino]-6-chloro-2-quinozolinyl]-4-piperidine-carboxylic acid, mono-sodium salt; (+)-cis- 5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propyl indole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo (4,3-d)pyrimidin-7-one; 1-[4-[(1,3-benzodioxol-5-ylmethyl)amino]-6-chloro-2-quinazolinyl]4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; WO 96/26940); Pharmaprojects No. 5069 (Schering Plough); GF-196960 (Glaxo Wellcome); E-8010 and E-4010 (Eisai); Bay-38-3045 & 38-9456 (Bayer); FR 229934 and FR 226807 (Fujisawa); and Sch-51866.

Preferably the PDEV inhibitor is selected from sildenafil, tadalafil, vardenafil, DA-8159 and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one. Most preferably, the PDE5 inhibitor is sildenafil and pharmaceutically acceptable salts thereof. Sildenafil citrate is a preferred salt.

The compounds of the present invention may be administered in combination with a V1a antagonist. Thus, in a further aspect of the invention, there is provided a pharmaceutical product containing a progesterone receptor antagonist and one or more V1a antagonists as a combined preparation for simultaneous, separate or sequential use in the treatment of endometriosis.

A suitable vasopressin V1a receptor antagonist is, for example, (4-[4-benzyl-5-(4-methoxy-piperidin-1-ylmethyl)-4H-[1,2,4]triazol-3-yl]-3,4,5,6-tetrahydro-2H-[1,2']bipyridinyl), Example 26 in WO 2004/37809. A further example of a suitable vasopressin V1a receptor antagonist is 8-chloro-5-methyl-1-(3,4,5,6-tetrahydro-2H-[1,2']bipyridinyl-4-yl)-5,6-dihydro-4H-2,3,5,10b-tetraazo-benzo[e]azulene, or a pharmaceutically acceptable salt or solvate thereof, i.e., Example 5 in WO 04/074291.

Further examples of vasopressin V1a receptor antagonists for use with the invention are: SR49049 (Relcovaptan), atosiban (Tractocile®), conivaptan (YM-087), VPA-985, CL-385004, Vasotocin, OPC21268, and the V1a receptor antagonists in WO 01/58880.

The compounds of the present invention may be administered in combination with an alpha adrenergic receptor antagonist (α-adrenoceptor blocker, α-receptor blocker or α-blocker). Thus, in a further aspect of the invention, there is provided a pharmaceutical product containing a progesterone receptor antagonist and one or more alpha adrenergic receptor antagonists as a combined preparation for simultaneous, separate or sequential use in the treatment of endometriosis.

$\alpha_1$-Adrenergic receptor antagonists useful for the present invention include, but are not limited to, terazosin (U.S. Pat. No. 4,026,894), doxazosin (U.S. Pat. No. 4,188,390), prazosin (U.S. Pat. No. 3,511,836), bunazosin (U.S. Pat. No. 3,920,636), alfuzosin (U.S. Pat. No. 4,315,007), naftopidil (U.S. Pat. No. 3,997,666), tamsulosin (U.S. Pat. No. 4,703,063), silodosin (U.S. Pat. No. 5,387,603), phentolamine and phentolamine mesylate (U.S. Pat. No. 2,503,059), trazodone (U.S. Pat. No. 3,381,009), indoramin (U.S. Pat. No. 3,527,761), phenoxybenzamine (U.S. Pat. No. 2,599,000), rauwolfa alkaloids (Rauwolfia serpentine), Recordati 15/2739 (WO 93/17007), SNAP 1069 (WO 94/08040, e.g., compound 9), SNAP 5089 (WO 94/10989), RS17053 (U.S. Pat. No. 5,436,264), SL 89.0591 (EP 435749), and abanoquil (EP 100200); the compounds disclosed in WO 03/076427, in particular, 5-cyclopropyl-7-methoxy-2-(2-morpholin-4-ylmethyl-7,8-dihydro[1,6]-naphthyridin-6(5H)-yl)-4(3H)-quinazolinone (Example 11), and the compounds disclosed in WO 98/30560, in particular, 4-amino-6,7-dimethoxy-2-(5-methanesulfonamido-1,2,3,4-tetrahydroisoquinol-2-yl)-5-(2-pyridyl)quinazoline (Example 19); and pharmaceutically acceptable derivatives thereof. Preferred α-adrenergic receptor antagonists are doxazosin, 5-cyclopropyl-7-methoxy-2-(2-morpholin-4-ylmethyl-7,8-dihydro[1,6]-naphthyridin-6(5H)-yl)-4(3H)-quinazolinone and 4-amino-6,7-dimethoxy-2-(5-methanesulfonamido-1,2,3,4-tetrahydroisoquinol-2-yl)-5-(2-pyridyl)quinazoline and pharmaceutically acceptable derivatives thereof. The mesylate salt of 4-amino-6,7-dimethoxy-2-(5-methanesulfonamido-1,2,3,4-tetrahydroisoquinol-2-yl)-5-(2-pyridyl) quinazoline is preferred (WO 01/64672).

$\alpha_2$-Adrenergic receptor antagonists suitable for the present invention include dibenamine (DE 824208), tolazoline (U.S. Pat. No. 2,161,938), trimazosin (U.S. Pat. No. 3,669,968), efaroxan (EP 71368), yohimbine (Goldberg, et al., Pharmacol. Rev., 35, 143-180 (1987)), idazoxan (EP 33655), and clonidine (U.S. Pat. No. 3,202,660).

Non-selective α-adrenergic receptor antagonists suitable for the present invention include dapiprazole (U.S. Pat. No. 4,252,721).

The compounds of the present invention may be administered in combination with a 5-alpha reductase inhibitor. Thus, in a further aspect of the invention, there is provided a pharmaceutical product containing a progesterone receptor antagonist and one or more 5-alpha reductase inhibitors as a combined preparation for simultaneous, separate or sequential use in the treatment of endometriosis.

5-alpha reductase inhibitors include inhibitors of 5-alpha reductase isoenzyme 2. Suitable compounds for use in the present invention are PROSCAR® (finasteride, U.S. Pat. Nos. 4,377,584 and 4,760,071), compounds described in WO 93/23420, EP 0572166, WO 93/23050, WO 93/23038, WO 93/23048, WO 93/23041, WO 93/23040, WO 93/23039, WO 93/23376, WO 93/23419, EP0572165, and WO 93/23051.

The compounds of the present invention may be administered in combination with an agent which lowers estrogen levels, or which antagonises the estrogen receptor. Thus, in a further aspect of the invention, there is provided a pharmaceutical product containing a progesterone receptor antagonist and one or more agents that lower estrogen levels, or antagonise the estrogen receptor, as a combined preparation for simultaneous, separate or sequential use in the treatment of endometriosis.

Agents which lower estrogen levels include gonadotropin releasing hormone (GnRH) agonists, GnRH antagonists and estrogen synthesis inhibitors. Agents which antagonise the estrogen receptor, i.e., estrogen receptor antagonists, include anti-estrogens.

GnRH agonists suitable for the present invention include leuprorelin (Prostap—Wyeth), buserelin (Suprefact—Shire), goserelin (Zoladex—Astra Zeneca), triptorelin (Decapeptyl—Ipsen), nafarelin (Synarel—Searle), deslorelin (Somagard—Shire), and histrelin/supprelin (Ortho Pharmaceutical Corp/Shire).

GnRH antagonists suitable for the present invention include teverelix (also known as antarelix), abarelix (Plenaxis—Praecis Pharmaceuticals Inc.), cetrorelix (Cetrotide—ASTA Medica), and ganirelix (Orgalutran—Organon).

Anti-estrogens suitable for the present invention include tamoxifen, Faslodex (Astra Zeneca), idoxifene (see Coombes, et al., (1995) Cancer Res. 55, 1070-1074), raloxifene or EM-652 {Labrie, et al., (2001) J. Steroid Biochem., Mol. Biol., 79, 213}.

Estrogen synthesis inhibitors suitable for the present invention include aromatase inhibitors. Examples of aromatase inhibitors include formestane (4-OH androstenedione), exemestane, anastrozole (arimidex) and letroxole.

The compounds of the present invention may be administered in combination with an alpha-2-delta ligand. Thus, in a further aspect of the invention, there is provided a pharmaceutical product containing a progesterone receptor antagonist and one ore more alpha-2-delta ligands, as a combined preparation for simultaneous, separate or sequential use in the treatment of endometriosis.

Examples of alpha-2-delta ligands for use in the present invention are those compounds, or pharmaceutically acceptable salts thereof, generally or specifically disclosed in U.S. Pat. No. 4,024,175, particularly gabapentin, EP 641330, particularly pregabalin, U.S. Pat. No. 5,563,175, WO 97/33858, WO 97/33859, WO 99/31057, WO 99/31074, WO 97/29101, WO 02/085839, particularly [(1R,5R,6S)-6-(aminomethyl)bicyclo[3.2.0]hept-6-yl]acetic acid, WO 99/31075, particularly 3-(1-aminomethyl-cyclohexylmethyl)-4H-[1,2,4]oxadiazol-5-one and C-[1-(1H-tetrazol-5-ylmethyl)-cycloheptyl]-methylamine, WO 99/21824, particularly (3S,4S)-(1-aminomethyl-3,4-dimethyl-cyclopentyl)-acetic acid, WO 01/90052, WO 01/28978, particularly (1α,3α,5α)(3-amino-methyl-bicyclo[3.2.0]hept-3-yl)-acetic acid, EP 0641330, WO 98/17627, WO 00/76958, particularly (3S,5R)-3-aminomethyl-5-methyl-octanoic acid, WO 03/082807, particularly (3S,5R)-3-amino-5-methyl-heptanoic acid, (3S,5R)-3-amino-5-methyl-nonanoic acid and (3S,5R)-3-amino-5-methyl-octanoic acid, WO 04/039367, particularly (2S,4S)-4-(3-fluoro-phenoxymethyl)-pyrrolidine-2-carboxylic acid, (2S,4S)-4-(2,3-difluoro-benzyl)-pyrrolidine-2-carboxylic acid, (2S,4S)-4-(3-chlorophenoxy)proline and (2S,4S)-4-(3-fluorobenzyl) proline, EP 1178034, EP 1201240, WO 99/31074, WO 03/000642, WO 02/22568, WO 02/30871, WO 02/30881 WO 02/100392, WO 02/100347, WO 02/42414, WO 02/32736 and WO 02/28881.

Preferred alpha-2-delta ligands useful in the instant combinations include gabapentin, pregabalin, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)(3-amino-methyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S, 5R)-3-amino-5-methyl-nonanoic acid, (3S,5R)-3-amino-5-methyl-octanoic acid, (2S,4S)-4-(3-chlorophenoxy)praline, and (2S,4S)-4-(3-fluorobenzyl)praline, or pharmaceutically acceptable salts thereof.

Further preferred alpha-2-delta ligands for use in the combinations of the invention are (3S,5R)-3-amino-5-methyloctanoic acid, (3S,5R)-3-amino-5-methylnonanoic acid, (3R,4R,5R)-3-amino-4,5-dimethylheptanoic acid and (3R,4R,5R)-3-amino-4,5-dimethyloctanoic acid, and the pharmaceutically acceptable salts thereof.

Particularly preferred alpha-2-delta ligands for use in the combinations of the invention are selected from gabapentin, pregabalin, (1α,3α,5α)(3-amino-methyl-bicyclo[3.2.0]hept-3-yl)-acetic acid, (2S,4S)-4-(3-chlorophenoxy)proline and (2S,4S)-4-(3-fluorobenzyl)praline, or pharmaceutically acceptable salts thereof.

The compounds of the present invention may be administered in combination with an oxytocin receptor antagonist. Thus, there is provided a pharmaceutical product containing a progesterone receptor antagonist and one ore more oxytocin antagonists, as a combined preparation for simultaneous, separate or sequential use in the treatment of endometriosis.

Examples of oxytocin receptor antagonists suitable for the present invention are atosiban and barusiban (Ferring A B), TT-235 (Northwestern University), and AS-602305 (Serono S A).

The contents of the published applications mentioned above, and in particular the general formulae of the therapeutically active compounds of the claims and exemplified compounds therein, are incorporated herein in their entirety by reference thereto.

The compounds of the present invention may be administered in combination with one or more:
  (i) aromatase inhibitors;
  (ii) estrogen receptor agonists;
  (iii) angiogenesis inhibitors;
  (iv) VEGF inhibitors;
  (v) kinase inhibitors;
  (vi) protein farnesyl transferase inhibitors;
  (vii) androgen receptor modulators;
  (viii) androgen receptor agonists;
  (ix) androgen receptor antagonists;
  (x) prostanoid receptor agonists;
  (xi) prostanoid receptor antagonists;
  (xi) prostaglandin synthetase inhibitors;
  (xii) bioflavanoids;
  (xiii) alkylating agents;
  (xiv) microtubule modulators, e.g., microtubule stabilizers;
  (xv) topoisomerase I inhibitors;
  (xvi) metalloprotease inhibitors; or
  (xvii) progesterone modulators.

Thus, there is provided a pharmaceutical product containing a progesterone receptor antagonist and one or more:
  (i) aromatase inhibitors;
  (ii) estrogen receptor agonists;
  (iii) angiogenesis inhibitors;
  (iv) VEGF inhibitors;
  (v) kinase inhibitors;
  (vi) protein farnesyl transferase inhibitors;
  (vii) androgen receptor modulators;
  (viii) androgen receptor agonists;
  (ix) androgen receptor antagonists;
  (x) prostanoid receptor agonists;
  (xi) prostanoid receptor antagonists;
  (xi) prostaglandin synthetase inhibitors;
  (xii) bioflavanoids;
  (xiii) alkylating agents;
  (xiv) microtubule modulators, e.g., microtubule stabilizers;
  (xv) topoisomerase I inhibitors;
  (xvi) metalloprotease inhibitors; or
  (xvii) progesterone modulators, as a combined preparation for simultaneous, separate or sequential use in the treatment of endometriosis.

Generally, compounds of the invention will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form. Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang, *Expert Opinion in Therapeutic Patents,* 11 (6), 981-986 (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropylcellulose and hydroxypropylmethylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other ingredients may include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated, uncoated, or encapsulated.

The formulation of tablets is discussed in Lieberman, *Pharmaceutical Dosage Forms: Tablets,* Vol. 1,H. Lieberman (Marcel Dekker, New York, 1980).

Consumable oral films are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma, et al, *Pharmaceutical Technology On-line,* 25(2), 1-14, (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art. The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated {Finnin, J. Pharm. Sci., 88 (10), 955-958, (October 1 999)}.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing forming nanoparticles, high pressure homogenisation, or spray drying.

Capsules (gelatin or hydroxypropylmethylcellulose), blisters and cartridges for use in an inhaler may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 µg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubiliser. Most commonly used for these purposes are α-, β- and γ-cyclodextrins (WO 91/11172, WO 94/02518 and WO 98/55148).

Inasmuch as it may desirable to administer a combination of active compounds, for the purpose of treating a particular condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range <1 mg to 1000 mg, depending on the mode of administration. For example, oral administration may require a total daily dose of from <1 mg to 1000 mg, while an intravenous dose may only require from <1 mg to 500 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

As used herein, the terms "treating" and "to treat", mean to alleviate symptoms, eliminate the causation either on a temporary or permanent basis, or to prevent or slow the appearance of symptoms. The term "treatment" includes alleviation, elimination of causation (temporary or permanent) of, or prevention of symptoms and disorders associated with endometriosis and/or uterine leiomyoma. The treatment may be a pre-treatment as well as a treatment at the on-set of symptoms.

The compounds of the present invention may be tested in the screens set out below:

1.0 In Vitro Functional Assay for Progesterone Receptor (PR) Antagonism

The assay for PR antagonism takes advantage of the extensively reported modulation of alkaline phosphatase (AP) expression in human breast T47D mammary carcinoma cells {Beck, et al., (1993). The progesterone antagonist RU486 acquires agonist activity upon stimulation of cAMP signalling pathways. Proc. Natl. Acad. Sci., USA, 90, 4441-4445; Fensome, et al. (2002). New progesterone receptor antagonists: 3,3-disubstituted-5-aryloxindoles. Bioorg. Med. Chem. Lett., 12, 3487-3490; Zhang et al., (2002a). 6-Aryl-1,4-dihydro-benzo d 1,3 oxazin-2-ones: a novel class of potent, selective, and orally active nonsteroidal progesterone receptor antagonists. J. Med. Chem., 45, 4379-4382; Zhang et al., (2003). Novel 6-aryl-1,4-dihydrobenzo[d]oxazine-2-thiones as potent, selective, and orally active nonsteroidal progesterone receptor agonists. Bioorganic & Med. Chem. Lett., 13, 1313-1316; Zhang et al., (2002b). Potent nonsteroidal progesterone receptor agonists: synthesis and SAR study of 6-aryl benzoxazines. Bioorganic & Med. Chem. Lett., 12, 787-790; Zhang, et al., (2000). In vitro characterization of trimegestone: a new potent and selective progestin. Steroids 65, 637-643}. In the presence of progesterone, endogenous AP expression is induced in T47D cells and is inhibited by compounds possessing PR antagonistic activity. In the absence of progesterone any agonist activity is also observed as an induction of AP activity. By running the assay in two formats (±progesterone (P4)), compounds behaving as PR antagonists, agonists or partials can be identified.

The materials required to grow T47D cells and perform the progesterone-induced AP assay are outlined in Table 1.

TABLE 1

| Reagent | Supplier | Catalogue number |
|---|---|---|
| T47D human mammary carcinoma cells | American tissue culture collections; http://www.atcc.org/ | HTB-133 |
| Dimethyl sulphoxide (DMSO) | Sigma | D2650 |
| Dulbecco's modified Eagle's Medium (DMEM) | Gibco | 21969-035 |
| DMEM without phenol red | Gibco | 31053-028 |
| L-Glutamax, 200 mM | Gibco | 35050-038 |
| Charcoal stripped foetal calf serum (CS-FCS) | Globepharm | |
| Phosphate buffered saline (PBS) | Gibco | 14190-094 |
| Foetal bovine serum (FBS) | Sigma | F-7524 |
| BD Great EscAPe SEAP Chemiluminescence Detection kit | Fisher | K2041-1 |
| Progesterone (P4) | Sigma | P-6149 |
| Pluronic-F127 | Molecular Probes | P6867 |
| RU486 (Mifepristone) | Sigma | M-8046 |

Assay media (agonist format): DMEM without phenol red+5% CS-FCS+2 mM Glutamax. Assay media (antagonist format): DMEM without phenol red+5% CS-FCS+2 mM Glutamax+10 nM P4.

Briefly, T47D cells are grown by propagating in DMEM+10% FBS+2 mM Glutamax at 37° C./5% $CO_2$. At 80-90% confluence, the media is exchanged for phenol red free DMEM+5% CS-FCS (Assay media) and cultured for a further 24 hrs at 37° C./5% $CO_2$. T47D cells are then plated at $2.5 \times 10^4$ cells/well in 100 µL assay media in sufficient 96 well plates for the assay, in triplicates of each condition. For example, for a 5-point $IC_{50}$ curve on one compound, this is equivalent to 36 wells (2×18 wells, ±P4). These plates are then cultured for 24 hrs at 37° C./5% $CO_2$, leaving the outside wells blank by the addition of 200 µL PBS.

A 10 mM stock solution of compounds is prepared in DMSO (stored −20° C. in 10 µL aliquots). A 10 mM DMSO stock of RU486 is used as a standard pure PR antagonist. The compounds under investigation are added to assay medium, or a mixture of 0.05% pluronic acid in PBS, ±10 nM P4 to give a final concentration of 20 µM (i.e. 10 µL of the 10 mM stock to 5 µL assay medium ±10 nM P4). The samples are mixed thoroughly and serial dilutions of compounds from 10 □M to 0.1 nM in a 96 well plate, are prepared as follows:

The outside wells are left blank. Assay medium (225 µL) is added to one half of the plate (−P4), rows 3-8, and to the other half of the plate, assay medium +10 nM P4. To row 2, 250 µL of the top concentration of compound (20 µM±10 nM P4) is added. 25 µL of the 20 mM stock from row 2 is removed and added to the 225 µL of assay medium±10 nM P4 in row 3 and thoroughly mixed. This process is repeated down the plate to row 7 to achieve serial dilutions. The vehicle control is adjusted to contain 0.1% DMSO (i.e. 20 µL to 10 mL assay medium±10 nM P4 to give a concentration of 0.2% DMSO, add 250 µL to row 8).

|   | A | B | C | D | E | F | G | H |
|---|---|---|---|---|---|---|---|---|
| 1 | | | | | | | | |
| 2 | | | 20 µM − P4 | | | 20 µM + P4 | | |
| 3 | | | 2 µM | | | 2 µM | | |
| 4 | | | 200 nM | | | 200 nM | | |
| 5 | | | 20 nM | | | 20 nM | | |
| 6 | | | 2 nM | | | 2 nM | | |
| 7 | | | 0.2 nM | | | 0.2 nM | | |
| 8 | | | 0 nM vehicle | | | 0 nM vehicle | | |
| 9 | | | | | | | | |

100 μL of reagent from the dilution plates are transferred into the corresponding wells containing T47D cells assay medium, to give a final concentration of 10 μM to 0.1 nM compound (5 nM P4 antagonist format). The cells were incubated for 20 hrs at 37° C./5% $CO_2$., then media is removed, cells washed with PBS (200 μL) and lysed by placing the cells at −80° C. for 15 min and thawing at room temp. The freeze-thaw lysis is repeated, then PBS (50 μL) is added to each well. After 5 min, 30 μL of CSPD chemiluminescent substrate solution (final 0.06125 mM, 1.25 mM substrate solution×20 dilution with chemiluminescent enhancer, Great EscAPe SEAP Chemiluminescence Detection kit) is added to each well and mixed. The plates are incubated for 30 mins at room temperature and luminescence measured on a luminometer (VICTOR, Wallac).

The assay is performed in triplicate, in the agonist format (no exogenous P4), sigmoid fitting of the results is expressed as alkaline phosphatase induction (luminescence, arbitrary units or % with maximal progesterone response as 100%) by the test compounds. In this format, the $EC_{50}$ value is defined as the drug concentration required to produce a 50% induction of AP activity compared with 5 nM alone. Compounds with agonism, or partial agonism, that is an induction of AP activity which is sub-maximal to that induced by P4, are discarded in this way. In the antagonist format (5 nM P4), curve fitting the results is expressed as alkaline phosphatase inhibition by the test compounds. In this format, the $IC_{50}$ value is defined as the drug concentration required to produce a 50% inhibition of AP activity compared with 5 nM alone. For the purposes of compounds exemplified here, the IC50 values are less than 5 μM. In a preferred embodiment, the $IC_{50}$ value is less than 500 nM. In a more preferred embodiment, the $IC_{50}$ is less than 50 nM.

2.0 In Vitro Functional Assay for Glucocorticoid Activity (GR)

A SW1353 cell line, stably transfected with a full length GR construct and mouse mammary tumour virus (MMTV)-luciferase (Luc) reporter is used to perform the in vitro functional assay for glucocorticoid activity in this assay. The materials required to grow SW1353-MMTV-GR-Luc cells and perform the assay are indicated below, or outlined in Table 1.

SW1353-MMTV-GR-Luc cells, grown in DMEM containing 10% FBS, 2 mM glutamax and G418 (0.5 mg/mL, Gibco cat no. 10131-027), are plated at $0.5 \times 10^4$ cells/well (384 well black tissue culture clear bottom plates (Greiner cat no. 781091)) in 30 μL using a Multidrop micro and are incubated at 37° C., 5% $CO_2$ overnight. The culture media is replaced with assay media (30 μL; DMEM-phenol red containing 1 mg/L insulin, 2g/L lactalbumin hydrolysate and ascorbate (0.5 mg/L), added just prior to use) for at least 4 hrs prior to dosing. The assay is performed in two formats, an antagonist format in which test compounds are assessed for their ability to block the effect of 20 nM dexamethasone on luciferase activity, and an agonist format. A separate 384 plate is used to assess compounds in both formats.

A Genesis robot is used to dilute and stamp out ½ log unit (11 point) dose responses (starting at 1 μM final; 16 compounds/384 well plate) from a 96 well plate containing 4 mM stock concentrations of compounds to be tested. The compounds under investigation are diluted in to assay medium+3.75% DMSO, or a mixture of 0.05% pluronic acid in PBS. A dexamethasone and RU-486 (1 μM final) positive control are prepared from concentrated stocks. A MATRIX Platemate is used to transfer 10 μL of diluted compounds to plates and either 10 μL of media or standards, so that the final volume of the assay is 50 μL. The cells and compounds are incubated at 37° C., 5% $CO_2$ overnight. The Steady-Glo LuciLite reagent (Promega cat no. E2520) is then re-constituted and 30 μL added per well, left in the dark for 5 mins and then the plate is read on a Wallac luminescence counter. All data points are measured in duplicate.

In the agonist format, sigmoid fitting of the results, expressed as luciferase induction (% of maximal dexamethasone response) by the test compounds, is achieved and $EC_{50}$ value is determined. In the antagonist format, results are expressed as luciferase inhibition by the test compounds and an $IC_{50}$ value is determined.

3.0 In Vivo Assessment for Progesterone Receptor Antagonism Using the McPhail's Assay The classical quantitative assessment of progestogenic activity is the McPhail's assay, performed in the immature rabbit (McPhail, 1934).

All of the compounds according to the formula (I) can be prepared by conventional routes such as the procedures described in the general methods presented below, or by the specific methods described in the Examples section, or by similar methods thereto. The present invention also encompasses any one or more of these processes for preparing the compounds of formula (I), in addition to any novel intermediates used therein.

In the following general methods, $R^1$ to $R^8$, X, Y and a are as previously defined for a compound of formula (I) unless otherwise stated.

In Scheme 1 below, compounds of formula (I) may be prepared by the oxidation of a compound of formula (II). The oxidation proceeds via the sulphoxide (Ia) (a=1) through to the sulphone (Ib) (a=2).

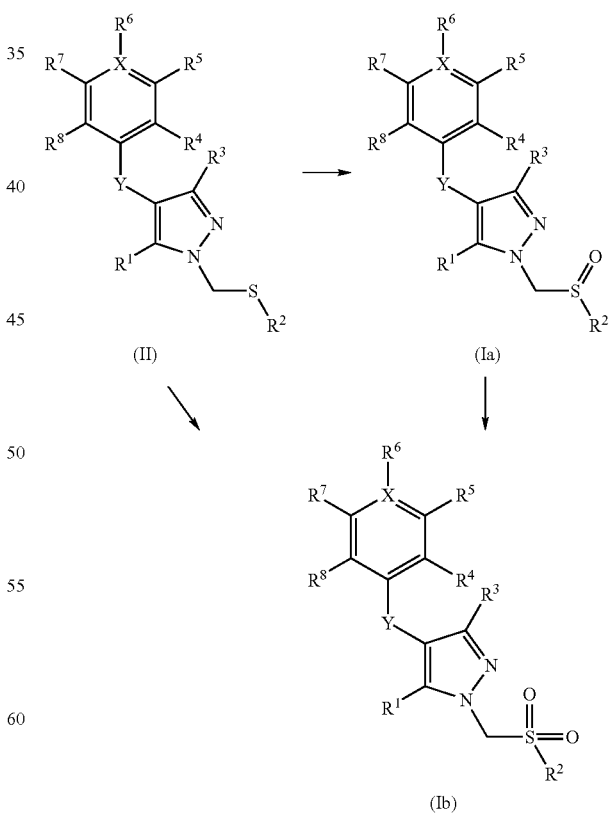

Scheme 1

Many suitable oxidants and oxidising conditions are available in the scientific literature for converting sulphides to sulphoxides and sulphones. In particular, a preferred method is reaction with Oxone® in a solvent mixture such as methanol and water, at temperatures from ambient to reflux.

In Scheme 2 below, sulphides of formula (II) may be prepared by alkylation of pyrazoles, of formula (III), with compounds of formula (IV) (where $L^1$ is a leaving group, such as chlorine), and a suitable base, such as potassium tert-butoxide, in a suitable solvent, such as dimethoxyethane, at temperatures from ambient to reflux.

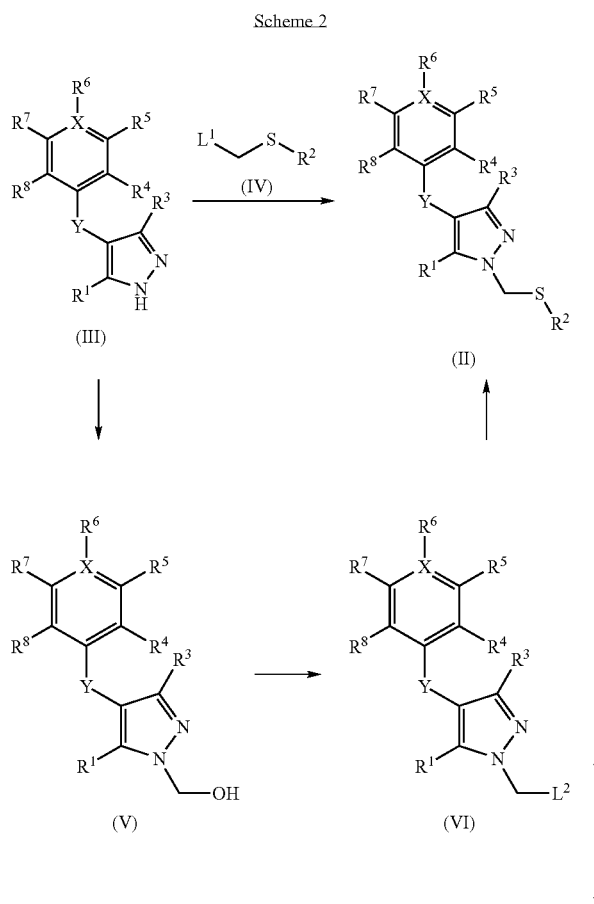

Alternatively, sulphides of formula (II) may be prepared from compounds of formula (VI), where $L^2$ is a leaving group such as chlorine, by reaction with a thiolate salt of formula $R^2SM^+$, where $M^+$ is a cation such as $Na^+$, $K^+$ or $Cu^+$, in a suitable solvent, such as 1,4-dioxane, dimethylformamide or tetrahydrofuran. The compounds of formula (IV) can be prepared by activation of the hydroxyl of compounds of formula (V), to form a leaving group $L^2$. Preferably when $L^2$ is chlorine this may be achieved with thionyl chloride in dichloromethane. The compounds of formula (V) may be prepared by reaction of compounds of formula (III) with a source of formaldehyde, such as aqueous formaldehyde. When $R^1 \neq R^3$ in compounds of formula (III) then the resultant compounds of formula (II), (V) and (VI) can exist as optionally separable regioisomers with $R^1$ and $R^3$ transposed.

In Scheme 3 below, compounds of formula (III), when Y is O, may be prepared by the condensation of a compound of formula (VII) with hydrazine or a salt or hydrate thereof, optionally in the presence of an acid or a base. The base is preferably a tertiary amine base, such as triethylamine. The acid is preferably acetic acid. In a typical procedure, a solution of the compound of formula (VII) in a suitable solvent, such as ethanol, is treated with hydrazine, or the salt or hydrate thereof, and, if used, the appropriate acid or base, at a temperature of from room temperature to the reflux temperature of the solvent. In a preferred procedure, the reaction mixture in ethanol and acetic acid is heated under reflux.

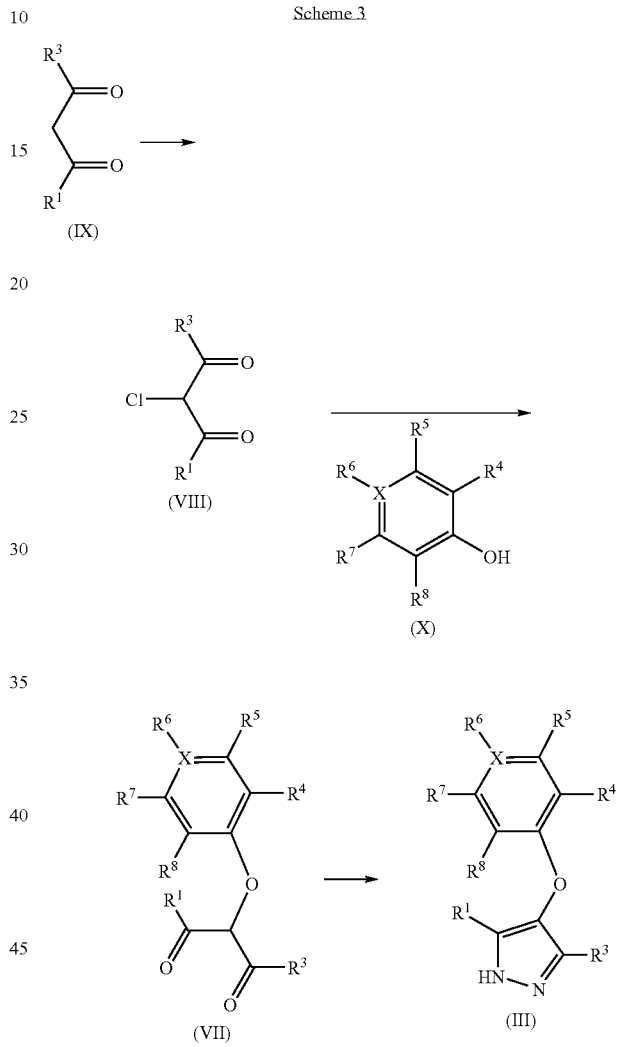

Compounds of formula (VII) may be prepared by reaction of compounds of formula (VIII) with compounds of formula (X) and a suitable base, such as cesium carbonate, in a solvent such as acetone. Compounds of formula (VIII) are either commercially available or may be prepared by the reaction of a compound of formula (IX) with a chlorinating reagent. In a typical procedure, a cooled solution of the compound of formula (IV), in a suitable solvent, such as acetonitrile, is treated first with tetrabutylammonium bromide and chlorotrimethylsilane, and then dry dimethylsulphoxide.

Functional equivalents of compounds of formula (VII) may also be used in this reaction. These include compounds of formula (XI) or (XII) below, in which $L^3$ is a suitable leaving group; preferably —$N(C_1-C_6alkyl)_2$, more preferably —$N(CH_3)_2$.

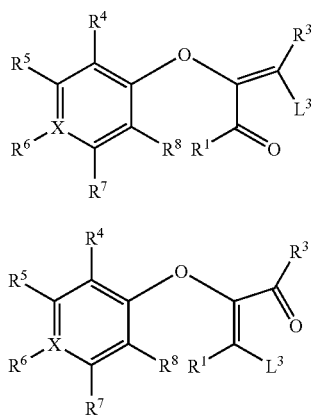

Thus, a compound of formula (III) may be prepared by the condensation of a compound of formula (XI) or (XII), with hydrazine, or a salt or hydrate thereof, optionally in the presence of an acid or a base (the base preferably being a tertiary amine base, such as triethylamine, and the acid preferably being acetic acid). In a typical procedure, a solution of the compound of formula (XI) or (XII), in a suitable solvent (such as ethanol) is treated with hydrazine, or the salt or hydrate thereof, and, if used, the appropriate acid or base, at a temperature of from room temperature to the reflux temperature of the solvent. In a preferred procedure, the reaction mixture is heated under reflux. Compounds of formula (XI) or (XII), are particularly suitable for the synthesis of compounds of formula (I), in which $R^1$, or $R^3$, respectively, represents H.

Compounds of formula (XI) in which $R^1$ is H, and compounds of formula (XII) in which $R^3$ is H, and $L^3$ is dimethylamino, may be prepared by the reaction of a compound of formula (XIII), below, with dimethylformamide dimethylacetal at an elevated temperature, preferably at about 100° C.

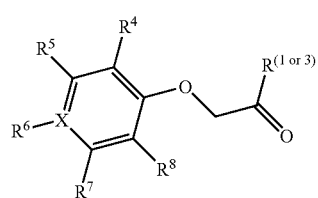

Compounds of formula (XIII) are either commercially available or may be prepared by the reaction of a compound of formula (XIV), with a phenol of formula (X).

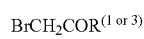

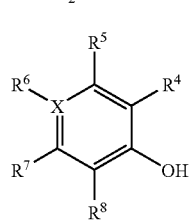

In a typical procedure, a solution of the compound of formula (XIV), in a suitable solvent, such as acetone, is treated with a suitable base, such as caesium carbonate, and the compound of formula (X). In a preferred procedure, the reaction mixture is heated, for example under reflux. Optionally, a nucleophilic catalyst, such as sodium iodide or tetrabutylammonium iodide, may be added.

In Scheme 4 below, compounds of formula (III), wherein Y represents $CH_2$, may be prepared in a similar method to that described in Scheme 3, by condensation of a compound of formula (XV) with hydrazine. Compounds of formula (XV) may be prepared by alkylation of compounds of formula (IX) with compounds of formula (XVI), where $L^4$ is a leaving group such as chlorine, bromine or iodine, with a suitable base such as sodium hydride or potassium tert-butoxide, in a suitable solvent such as tetrahydrofuran or 2-butanone at temperatures from ambient to reflux.

Scheme 4

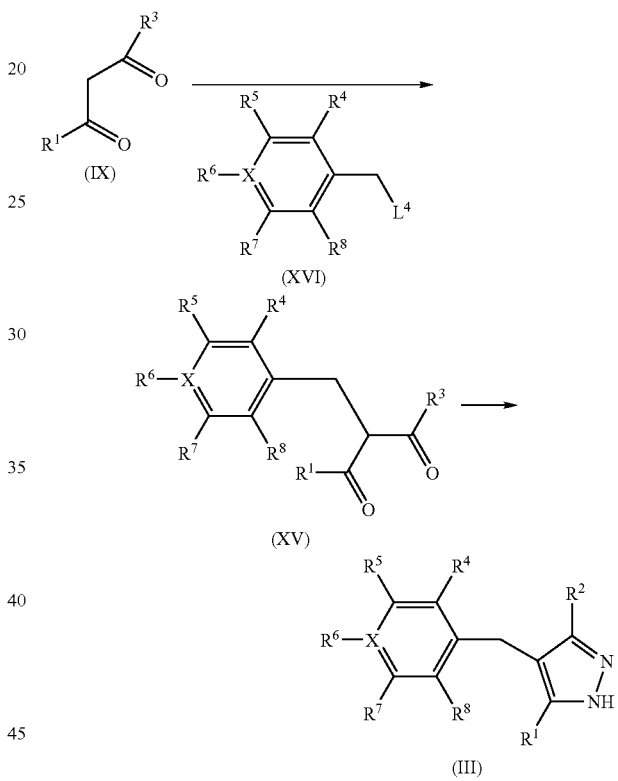

It will be appreciated by those skilled in the art that, in many cases, compounds of the formula (I) may be converted into other compounds of the formula (I) by functional group transformations.

Thus, according to a further aspect of the invention, there is provided a process for preparing compounds of Formula (I) wherein a=1, which comprises oxidising a compound of formula (II).

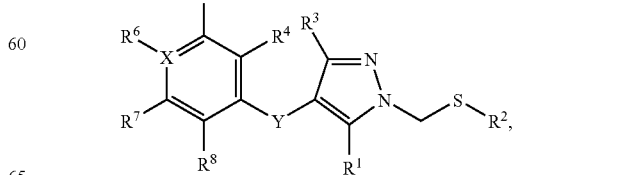

wherein $R^1$-$R^8$, X and Y are as defined above.

Furthermore, there is provided a process for preparing compounds of Formula (I) wherein a=2, which comprises oxidising a compound of formula (II).

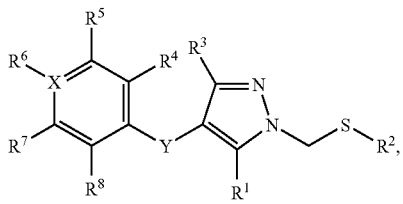

(II)

wherein $R^1$-$R^8$, X and Y are as defined above.

Furthermore, there is provided a process for preparing compounds of Formula (I) wherein a=2, which comprises oxidising a compound of formula (Ia).

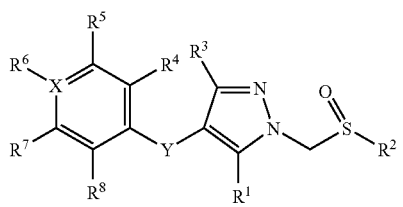

(Ia)

wherein $R^1$-$R^8$, X and Y are as defined above.

Also within the scope of the invention are intermediates of formula (II), as hereinbefore defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of compound of formula (II), that provides the best combination of features for this purpose. Such features include the melting point, solubility, processability and yield of the intermediate form and the resulting ease with which the product may be purified on isolation.

The compounds of the invention may have the advantage that they are more potent, have a longer duration of action, have a broader range of activity, are more stable, have fewer side effects or are more selective, or have other more useful properties than the compounds of the prior art.

Thus the invention provides:

(i) a compound of formula (I) or a pharmaceutically acceptable derivative thereof;

(ii) a process for the preparation of a compound of formula (I) or a pharmaceutically acceptable derivative thereof;

(iii) a pharmaceutical formulation including a compound of formula (I) or a pharmaceutically acceptable derivative thereof, together with a pharmaceutically acceptable excipients, diluent or carrier;

(iv) a compound of formula (I) or a pharmaceutically acceptable derivative or composition thereof, for use as a medicament;

(v) the use of a compound of formula (I) or of a pharmaceutically acceptable derivative or composition thereof, for the manufacture of a medicament for the treatment of endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome;

(vi) use as in (v) where the disease or disorder is endometriosis and/or uterine fibroids (leiomyomata);

(vii) a method of treatment of a mammal to treat endometriosis, uterine fibroids (leiomyomata), menorrhagia, adenomyosis, primary and secondary dysmenorrhoea (including symptoms of dyspareunia, dyschexia and chronic pelvic pain), chronic pelvic pain syndrome including treating said mammal with an effective amount of a compound of formula (I) or with a pharmaceutically acceptable derivative or composition thereof;

(viii) a method as in (vii) where the disease or disorder is endometriosis and/or uterine fibroids (leiomyomata);

(ix) intermediates of the formulae (II);

The following preparations and examples illustrate the preparation of the compounds of formula (I).

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

The following abbreviations have been used throughout:
HRMS high resolution mass spectrometry;
LRMS low resolution mass spectrometry;
hplc high performance liquid chromatography;
nOe nuclear Overhauser effect;
m.p melting point;
$CDCl_3$ deuterochloroform;
$D_6$-DMSO deuterodimethylsulphoxide;
$CD_3OD$ deuteromethanol The Preparations and Examples that follow illustrate the invention but do not limit the invention in any way. All starting materials are available commercially or described in the literature. All temperatures are in 0° C. Flash column chromatography was carried out using Merck silica gel 60 (9385). Thin layer chromatography (TLC) was carried out on Merck silica gel 60 plates (5729). $R_f$ represents the distance travelled by a compound divided by the distance travelled by the solvent front on a TLC plate. Melting points were determined using a Gallenkamp MPD350 apparatus and are uncorrected. NMR was carried out using a Varian-Unity Inova 400 MHz NMR spectrometer or a Varian Mercury 400 MHz NMR spectrometer. Mass spectroscopy was carried out using a Finnigan Navigator single quadrupole electrospray mass spectrometer or a Finnigan aQa APCl mass spectrometer.

Where it is stated that compounds were prepared in the manner described for an earlier Preparation or Example, the skilled person will appreciate that reaction times, number of equivalents of reagents and reaction temperatures may be modified for each specific reaction, and that it may nevertheless be necessary or desirable to employ different work-up or purification conditions.

Preparation 1: 1,3-Dicyclopropyl-propane-1,3-dione

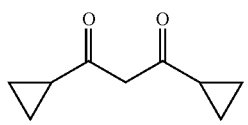

Methylcyclopropanecarboxylate (20.2 ml, 286.3 mmol) was added to a stirred solution of 1-cyclopropylethanone (9 ml, 152.4 mmol) in dimethylsulfoxide (25 ml). Sodium methoxide powder (10.8 g, 200 mmol) was added, and the reaction was stirred at 55° C. for 8 hours. The mixture was cooled, diluted with toluene, neutralised with 6M hydrochloric acid, and then extracted with toluene. The combined extracts were washed with sodium carbonate, dried over magnesium sulphate and evaporated in vacuo to provide the title compound (14.9 g, 78%) as a mixture 2:1 enol:ketone forms. $^1$H NMR (CDCl$_3$, 400 MHz): δ=0.79-0.87 (m, 4H), 0.98-1.01 (m, 4H), 1.46-1.51 (m, 2H-enol), 1.93-1.97 (m, 2H-keto), 3.70 (s, 2H-keto), 5.65 (s, 1H-enol); LRMS: APCl$^+$: m/z 153 [MH$^+$]; APCl$^-$ m/z 151 [M–H]$^-$.

Preparation 2: 3-Oxobutanoic acid

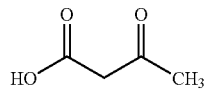

Sodium hydroxide (37.9 g, 947 mmol) was dissolved in water (770 ml) and added to a solution of 3-oxo-butanoic acid methyl ester (100 g, 861 mmol), at room temperature, over 20 minutes. The reaction mixture was stirred for 18 hours, after which time it was quenched with ammonium sulfate (700 g) and acidified slowly with a solution of concentrated hydrochloric acid (21.5 ml) in water (250 ml), with ice cooling. The reaction mixture was then extracted with diethyl ether (6×200 ml) and the combined organic extracts were dried over magnesium sulphate, and concentrated under reduced pressure to provide the title compound (58.2 g, 60%) as a pale yellow oil, which was a mixture of keto:enol tautomers. $^1$H NMR (400 MHz, CDCl$_3$): δ=2.00 (s, 3H-enol), 2.30 (s, 3H-keto), 3.51 (s, 2H-keto), 5.02 (s, 1H-enol).

Preparation 3: 1-Cyclopropyl-1,3-butanedione

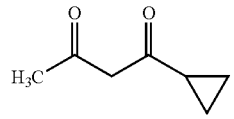

Magnesium turnings (3.04 g, 125 mmol), suspended in methanol (145 ml), were heated to reflux under nitrogen for 1 hour, then cooled to room temperature and the β-keto acid from Preparation 2 (25.5 g, 250 mmol) dissolved in methanol (25 ml) was added dropwise, with ice-cooling. The reaction mixture was stirred for 1 hour, at room temperature, and then the solvent was removed under reduced pressure to give the magnesium salt of the acid. Meanwhile, cyclopropane-carboxylic acid (9.91 ml, 125 mmol) was dissolved in dimethylformamide (200 ml). Carbonyldiimidazole (22.4 g, 138 mmol) was then added portionwise, under nitrogen, at 0° C. This reaction mixture was stirred for 1.5 hours, and then the magnesium salt from above was added as a solution in N,N-dimethylformamide (100 ml) at 0° C. The reaction mixture was allowed to stir at room temperature for 92 hours, and then it was poured into 2M aqueous hydrochloric acid (85 ml), followed by dilution with water (170 ml). The mixture was extracted with diethyl ether (6×200 ml), and the combined organic extracts were then washed with brine (3×200 ml), dried over magnesium sulphate and concentrated under reduced pressure. The residual orange oil was purified by flash chromatography on silica gel eluting with pentane:diethyl ether (100:0 then 90:10 then 80:20, by volume) to provide the title compound (7.39 g, 24%) as a yellow oil. $^1$H NMR (400 MHz, CDCl$_3$): δ=0.83-0.95 (m, 2H), 1.06-1.10 (m, 2H), 1.54-1.63 (m, 1H), 2.00 (s, 3H); LRMS (electrospray): m/z 149 [MNa$^+$].

Preparation 4:
2-Chloro-1,3-dicyclopropyl-1,3-propanedione

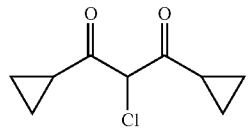

Chlorotrimethylsilane (36 ml, 296 mmol) was added dropwise to a stirred solution of tetrabutylammonium bromide (1.54 g, 5 mmol) in dry acetonitrile (100 ml) at room temperature, under nitrogen. The resulting solution was cooled in ice, and the diketone of Preparation 1 (15 g, 98.7 mmol), as a solution in acetonitrile (30 ml), was added dropwise, followed by dry dimethylsulphoxide (20 ml, 296 mmol). The reaction was allowed to warm slowly to room temperature, and stirred for 18 hours. The mixture was diluted with water, stirred for 10 minutes and then extracted with diethyl ether (50 ml). The layers were separated, and the aqueous layer was extracted again with diethyl ether. The organic layers were combined, dried over magnesium sulphate, filtered and concentrated under reduced pressure. The crude product was purified by column chromatography on silica gel eluting with pentane:diethyl ether (20:1, by volume) to provide the title compound as a 2:7 mixture of keto:enol tautomers (12.1g, 66%). $^1$H NMR (400 MHz, CDCl$_3$): δ=1.01-1.07 (m, 4H), 1.16-1.21 (m, 4H), 2.23-2.28 (m, 2H-keto), 2.39-2.44 (m, 2H-enol), 5.07 (s, 1H-keto); LRMS: APCl$^+$: m/z 187 [MH$^+$]; APCl$^-$ m/z 185 [M–H]$^-$.

Preparations 5 to 8

The compounds of the following preparations having the general formula:

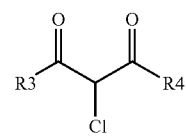

were prepared by a similar method to that of Preparation 4, using the appropriate diketone as starting material.

| Prep No | R3, R4 | Analytical Data |
|---|---|---|
| 5 | Me, cPr | $^1$H NMR(400MHz, CDCl$_3$): δ=1.01-1.04(m, 2H), 1.14-1.20(m, 2H), 2.27(s, 3H), 2.43(m, 1H); LRMS: APCl$^+$: m/z 161[MH$^+$]; APCl$^-$ m/z 159[M–H]$^-$; (62% yield). |
| 6 | Et, Et | $^1$H-NMR(400MHz, CDCl$_3$): δ=1.12(t, 6H), 2.59(q, 4H), 4.77(s, 0.2H, diketone), 15.50(s, 0.8H, enol); LRMS(thermospray): m/z 180[MNH$_4$$^+$]; (15% yield). |
| 7 | tBu, tBu | $^1$H-NMR(400MHz, CDCl$_3$): δ=1.25(brs, 18H), 5.65(s, 1H); LRMS APCl$^-$ m/z 217[M–H]$^-$; (95% yield). |
| 8 | Me, tBu | $^1$H NMR(400MHz, CDCl$_3$): δ=1.25(brs, 9H), 2.25(s, 3H), 5.65(s, 1H); LRMS: APCl$^+$: m/z 177[MH$^+$]; APCl$^-$ m/z 159[M–H]$^-$; (70% yield). |

Preparation 9: 4-(3,5-Dicyclopropyl-1H-pyrazol-4-yloxy)-benzonitrile

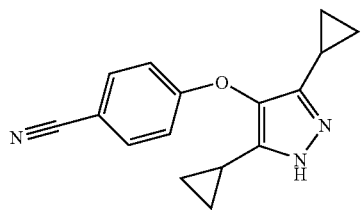

Step 1: A mixture of chlorodiketone from Preparation 4 (48.2 g, 258 mmol), 4-cyanophenol (37 g, 310 mmol), cesium carbonate (101 g, 310 mmol) and acetone (1200 ml) was heated under reflux for 4 hours. The solvent was then evaporated under reduced pressure and the residue was partitioned between diethyl ether (1000 ml) and water (300 ml). The layers were separated and the organic layer was washed with water (2×500 ml). The organic layer was dried over magnesium sulphate, filtered and concentrated under reduced pressure. The crude product was purified by column chromatography on silica gel eluting with pentane:dichloromethane in a ratio of 1:1 until product began to elute, and then in a ratio of 1:2 to complete elution. The solvent was evaporated to provide the intermediate 4-(1-cyclopropanecarbonyl-2-cyclopropyl-2-oxo-ethoxy)-benzonitrile as a solid (44.1 g). This intermediate can be optionally purified by chromatography on silica gel eluting with ethyl acetate:pentane mixtures or taken on to Step 2 as crude diketone.

Step 2: The 4-(1-cyclopropanecarbonyl-2-cyclopropyl-2-oxo-ethoxy)-benzonitrile (44 g, 162 mmol) was dissolved in acetic acid (500 ml). A solution of hydrazine hydrate (8.7 ml, 179 mmol) in ethanol (50 ml) was then added at room temperature and the reaction mixture was heated to 90° C. for approximately 3 hours. The solvents were then evaporated under reduced pressure and the residues were partitioned between diethyl ether (600 ml) and dilute aqueous ammonium hydroxide (25 ml concentrated ammonium hydroxide in 500 ml water), and the layers were separated. The aqueous layer was further extracted with diethyl ether (3×200 ml) and the combined organic layers were washed with water (2×50 ml), dried over magnesium sulphate, filtered and concentrated under reduced pressure. The solid was slurried in diisopropyl ether (50 ml), filtered and rinsed with diisopropyl ether (2×30 ml) and pentane (2×100 ml) to provide the title compound (39.5 g, 58%) as a colourless solid. $^1$H-NMR (400 MHz, CDCl$_3$): δ=0.76-0.81 (m, 8H), 1.59-1.65 (m, 2H), 7.01 (d, 2H), 7.60 (d, 2H); LRMS: APCl$^+$: m/z 266 [MH$^+$]; APCl$^-$: m/z 264 [M–H]$^-$.

Preparations: 10 to 24

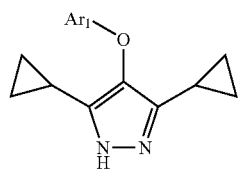

Compounds of the general formula above were prepared by a using a method similar to Preparation 9 using the chlorodiketone from Preparation 4, and the appropriate phenol (Ar$_1$OH available commercially, or from Preparations 42 or 45) as the starting materials.

| Prep No | Ar$_1$- | Analytical Data |
|---|---|---|
| 10 | ![H3C, CN substituted phenyl] | $^1$H-NMR(400 MHz, CDCl$_3$): δ=0.75-0.86(m, 8H), 1.59-1.66(m, 2H), 2.51(s, 3H), 6.81(d, 1H), 6.87(s, 1H), 7.52(d, 1H); LRMS: APCl$^+$: m/z 280[MH$^+$]; APCl$^-$: m/z 278[M–H]$^-$ (45% yield) |
| 11 | ![H3C, CN, CH3 substituted phenyl] | $^1$H-NMR(400 MHz, CDCl$_3$): δ=0.75-0.81(m, 8H), 1.60-1.66(m, 2H), 2.48(s, 6H), 6.67(s, 2H); LRMS: APCl$^+$: m/z 294[MH$^+$]; APCl$^-$: m/z 292 [M–H]$^-$. (55% yield) |
| 12 | ![Cl, CN substituted phenyl] | $^1$H-NMR(400 MHz, CDCl$_3$): δ=0.76-0.79(m, 4H), 0.82-0.85(m, 4H), 1.59-1.64(m, 2H), 6.93(d, 1H), 7.07(s, 1H), 7.55(brs, 1H), 7.60(d, 1H); LRMS: APCl$^+$: m/z 300[MH$^+$]; APCl$^-$: m/z 298 [M–H]$^-$. (50% yield) |
| 13 | ![F, CN substituted phenyl] | $^1$H-NMR(400 MHz, CDCl$_3$): δ=0.76-0.87(m, 8H), 1.63(m, 2H), 6.77(dd, 1H), 6.85(dd, 1H), 7.55(dd, 1H); LRMS: APCl$^+$: m/z 284[MH$^+$]; APCl$^-$ : m/z 282[M–H]$^-$. (48% yield) |

-continued

| Prep No | Ar₁- | Analytical Data |
|---|---|---|
| 14 | 4-chloro-3-cyanophenyl with tert-pentyl group | ¹H-NMR(400 MHz, CDCl₃): δ=0.76-0.85(m, 8H), 1.63(m, 2H), 6.83(d, 1H), 7.49(dd, 1H), 7.74(d, 1H); LRMS: APCl⁺: m/z 300 [MH⁺]; APCl⁻: m/z 298[M−H]⁻. (35% yield) |
| 15 | 4-fluoro-3-cyanophenyl with tert-pentyl group | ¹H-NMR(400 MHz, CDCl₃): δ=0.74-0.85(m, 8H), 1.63(m, 2H), 6.85(t, 1H), 7.40(d, 1H), 7.47(dd, 1H); LRMS: APCl⁺: m/z 284 [MH⁺]; APCl⁻ : m/z 282[M−H]⁻. (38% yield) |
| 16 | 4-methoxy-3-cyanophenyl with tert-pentyl group | ¹H-NMR(400 MHz, CDCl₃): δ=0.77-0.81(m, 8H), 1.64(m, 2H), 3.99(s, 3H), 6.75(d, 1H), 7.20(m, 2H); LRMS: APCl⁺: m/z 296 [MH⁺]. (25% yield) |
| 17 | 4-cyanonaphthyl with tert-pentyl group | ¹H-NMR(400 MHz, CDCl₃): δ=0.73-0.79(m, 8H), 1.63(m, 2H), 6.72(d, 1H), 7.67(t, 2H), 7.76(dd, 2H), 8.22(d, 1H), 8.50(d, 1H); LRMS: APCl⁺: m/z 316[MH⁺]; APCl⁻: m/z 314[M−H]⁻. (25% yield) |
| 18 | 8-cyanoquinolinyl with tert-pentyl group | ¹H-NMR(400 MHz, d-6 acetone): δ=0.72-0.80(m, 8H), 1.69(m, 2H), 2.81(s, 1H), 6.95(d, 1H), 7.79(dd, 1H), 8.20(d, 1H), 8.93 (dd, 1.76 Hz, 1H), 9.13(dd, 1H); LRMS: APCl⁺: m/z 317[MH⁺]; APCl⁻: m/z 315[M−H]⁻. (22% yield) |
| 19 | quinolinyl with tert-pentyl group | ¹H-NMR(400 MHz, CDCl₃): δ=0.77(d, 8H), 1.63(m, 2H), 6.66 (d, 1H), 7.62(t, 1H), 7.79(m, 1H), 8.20(d, 1H), 8.41(m, 1H), 8.72(d, 1H); LRMS: APCl⁺: m/z 292[MH⁺]; APCl⁻: m/z 290 [M−H]⁻. (35% yield) |
| 20 | 3-fluoro-4-chlorophenyl with tert-pentyl group | ¹H-NMR(400 MHz, CDCl₃): δ=0.74-0.85(m, 8H), 1.63(m, 2H), 6.7-6.8(m, 2H), 7.30(d, 1H); LRMS: APCl⁺: m/z 293[MH⁺]; APCl⁻: m/z 291[M−H]⁻. (43% yield) |
| 21 | 3,4-difluorophenyl with tert-pentyl group | ¹H-NMR(400 MHz, CDCl₃): δ=0.74-0.85(m, 8H), 1.63(m, 2H), 6.63(m, 1H), 6.75(m, 1H), 7.07(m, 1H); LRMS: APCl⁺: m/z 277[MH⁺]; APCl⁻: m/z 275 [M−H]⁻. (46% yield) |

| Prep No | Ar₁- | Analytical Data |
|---|---|---|
| 22 | 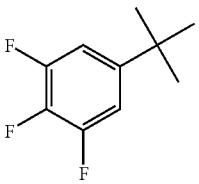 | ¹H-NMR(400 MHz, CDCl₃): δ=0.75-0.86(m, 8H), 1.64(m, 2H), 6.57(m, 2H), 8.96(s, 1H); LRMS: APCl⁺: m/z 295[MH⁺]; APCl⁻: m/z 293[M−H]⁻. (40% yield) |
| 23 | 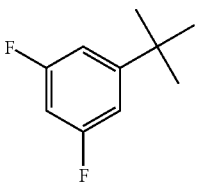 | ¹H-NMR(400 MHz, CDCl₃): δ=0.74-0.85(m, 8H), 1.63(m, 2H), 6.48(m, 3H), 7.4(brs, 1H); LRMS: APCl⁺: m/z 277[MH⁺]; APCl⁻: m/z 275[M−H]⁻. (41% yield) |
| 24 | 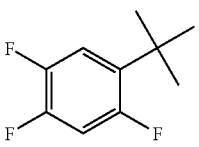 | ¹H-NMR(400 MHz, CDCl₃): δ=0.75-0.86(m, 8H), 1.64(m, 2H), 6.65(m, 1H), 7.02(m, 1H); LRMS: APCl⁺: m/z 295[MH⁺]; APCl⁻: m/z 293[M−H]⁻. (41% yield) |

Preparations: 25 to 26

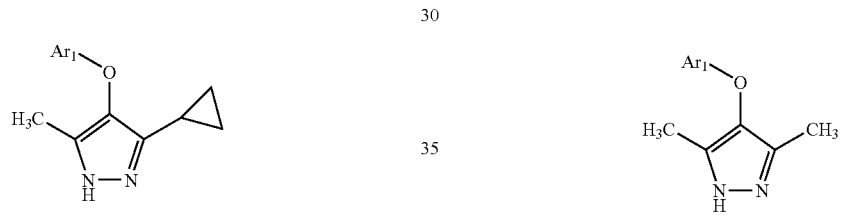

Compounds of the general formula above were prepared by a method similar to Preparation 9 using the chlorodiketone from Preparation 5, and the appropriate phenol (Ar₁OH available commercially, or from Preparations 42) as the starting materials.

Preparation 27

Compounds of the general formula above were prepared by a method similar to Preparation 9 using commercial 3-chloro-2,4-pentanedione and the appropriate phenol (Ar₁OH) as the starting materials.

| Prep No | Ar₁- | Analytical Data |
|---|---|---|
| 25 | 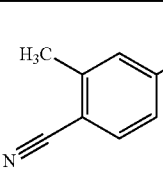 | ¹H-NMR(400 MHz, CDCl₃): δ=0.77-0.81(m, 4H), 1.66(m, 1H), 2.08(s, 3H), 2.50(s, 3H), 6.77(d, 1H), 6.84(s, 1H), 7.52(d, 1H); LRMS: APCl⁺: m/z 254[MH⁺]; APCl⁻: m/z 252[M−H]⁻; (71% yield) |
| 26 | 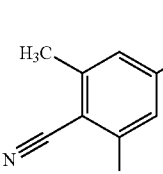 | ¹H-NMR(400 MHz, CDCl₃): δ=0.76-0.82(m, 4H), 1.67(m, 1H), 2.08(s, 3H), 2.47(s, 6H), 6.64(s, 2H); LRMS: APCl⁺: m/z 268 [MH⁺]; APCl⁻: m/z 266[M−H]⁻; (62% yield) |

| Prep No | Ar₁- | Analytical Data |
|---|---|---|
| 27 | (3-methyl-5-tBu-4-cyano-phenyl with H₃C and CH₃) | ¹H-NMR(400 MHz, CDCl₃): δ2.12(s, 6H), 2.47(s, 6H), 6.62 (s, 2H); LRMS: APCl⁺: m/z 242[MH⁺]; APCl⁻: m/z 240[M-H]⁻. (55% yield) |

Preparations: 28 to 29

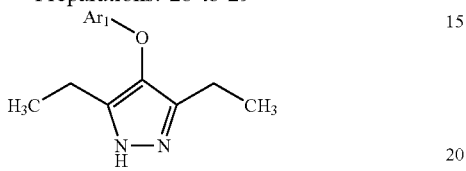

Compounds of the general formula above were prepared by a method similar to Preparation 9 using the chlorodiketone from Preparation 6, and the appropriate phenol (Ar₁OH) as the starting materials.

| Prep No | Ar₁- | Analytical Data |
|---|---|---|
| 28 | (4-cyano-tBu-phenyl) | ¹H-NMR(400 MHz, CDCl₃): δ=1.14(t, 6H), 2.48(q, 4H), 6.95 (d, 2H), 7.58(d, 2H), 10.31(brs, 1H); LRMS: APCl⁺: m/z 242 [MH⁺]; APCl⁻: m/z 240[M-H]⁻; (45% yield) |
| 29 | (3-methyl-5-tBu-4-cyano-phenyl with H₃C and CH₃) | ¹H-NMR(400 MHz, CDCl₃): δ=1.17(t, 6H), 2.47-2.50(m, 10H), 6.62(s, 2H); LRMS: APCl⁺: m/z 270[MH⁺]; APCl⁻ : m/z 268[M-H]⁻. (49% yield) |

Preparations: 30 to 31

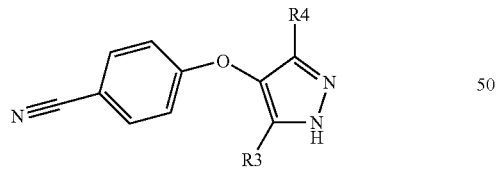

Compounds of the general formula above were prepared by a method similar to that described for Preparation 9 using 4-cyanophenol and the appropriate chlorodiketones described in Preparations 7 & 8 as the starting materials.

| Prep No | R3, R4 | Analytical Data |
|---|---|---|
| 30 | tBu, tBu | ¹H-NMR(400 MHz, CDCl₃): δ=1.2(s, 18H), 6.95(d, 2H), 7.58 (d, 2H), 10.0(brs, 1H); LRMS: APCl⁺: m/z 298[MH⁺]; APCl⁻ : m/z 296[M-H]⁻; (37% yield) |
| 31 | Me, tBu | ¹H-NMR(400 MHz, CDCl₃): δ=1.25(s, 9H), 2.0(s, 3H), 6.95(d, 2H), 7.58(d, 2H), 8.0(brs, 1H); LRMS: APCl⁺: m/z 256[MH⁺]; APCl⁻ : m/z 254[M-H]⁻; (44% yield) |

Preparation 32: 4-(3-Oxo-2-propionylpentyl)benzonitrile

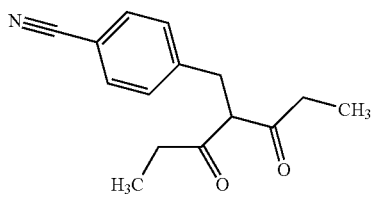

Sodium hydride (60% dispersion in oil, 3.43 g, 86 mmol) was added to a solution of 3,5-heptanedione (10 g, 78 mmol), in 2-butanone (200 ml), under nitrogen. A slight exotherm was observed during gas evolution. Sodium iodide (11.7 g, 78 mmol) was then added, followed by 4-cyanobenzyl bromide (15.29 g, 78 mmol) in 2-butanone (20 ml) and a precipitate was formed. The reaction mixture was heated at reflux for 16 hours. It was then filtered to remove the precipitate and concentrated under reduced pressure. The residue was stirred in dichloromethane (100 ml) and solid sodium bromide was removed by filtration. The dichloromethane filtrate was then washed with water (100 ml) and brine (100 ml). The organic layer was collected, dried over magnesium sulphate and concentrated under reduced pressure to give an orange solid. This was slurried in diethyl ether and filtered off to provide the title compound (11.01 g, 58%) as a pale yellow solid. $^1$H-NMR (400 MHz, CDCl$_3$): δ=0.98 (t, 6H), 2.29-2.35 (m, 2H), 2.42-2.52 (m, 2H), 3.19 (d, 2H), 3.97 (t, 1H), 7.25 (d, 2H), 7.56 (d, 2H); LRMS: APCI$^-$: m/z 242 [M–H].

Preparation 33: 4-[(3,5-Diethyl-1H-pyrazol-4-yl)methyl]benzonitrile

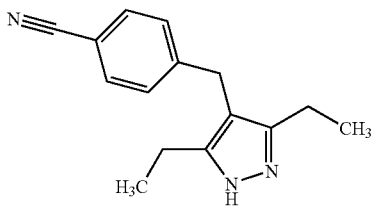

The title compound (4.9 g, 45%) was prepared by a similar method to that of Step 2 of Preparation 9 using the diketone from Preparation 32 and hydrazine as the starting materials. $^1$H-NMR (400 MHz, CDCl$_3$): δ=1.16 (t, 6H), 2.51 (q, 4H), 3.82 (s, 2H), 7.20 (d, 2H), 7.55 (d, 2H); LRMS: APCI$^+$: m/z 240 [MH$^+$].

Preparation 34: 4-(2-Cyclopropyl-2-oxoethoxy)-2,6-dimethylbenzonitrile

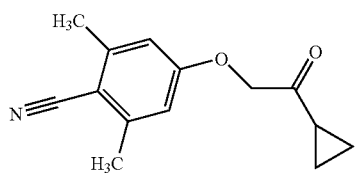

Bromine (12.84 ml, 250 mmol) was added dropwise, over 10 minutes, to an ice-cooled solution of cyclopropylmethylketone (21 g, 250 mmol), in methanol (150 ml), under nitrogen. The reaction was allowed to proceed with the internal temperature being kept under 10° C., until decolourisation was observed. The reaction mixture was then stirred at room temperature for a further 30 minutes. Water (75 ml) was added and the reaction mixture was stirred for a further 15 minutes. The mixture was diluted with water (225 ml) and extracted 4 times with diethyl ether (4×250 ml). The organic layers were combined, washed with a 10% aqueous solution of sodium bicarbonate (250 ml), followed by water (250 ml), followed by brine (250 ml), then dried over magnesium sulphate, filtered and concentrated under reduced pressure to provide 2-bromo-1-cyclopropylethanone.

Cesium carbonate (30.7 g, 111.16 mmol) was added to a solution of 4-hydroxy-2,6-dimethylbenzonitrile (15.27 g, 101.89 mmol), in acetone (377 ml). Then 2-bromo-1-cyclopropylethanone (15.1 g, 62.6 mmol), in acetone (100 ml), was added dropwise, over 5 minutes, to the suspension and the reaction mixture was heated at reflux for 1.5 hours. The reaction mixture was then concentrated under reduced pressure and the residue was partitioned between a saturated aqueous solution of potassium carbonate (300 ml) and dichloromethane (300 ml). The organic layer was separated and washed with brine (250 ml), dried over magnesium sulphate, filtered and then concentrated under reduced pressure. The crude product was purified by flash chromatography on silica gel eluting with dichloromethane:pentane (50:50 to 80:20, by volume) to provide the title compound (13.5 g, 64%) as a solid. $^1$H-NMR (400 MHz, CDCl$_3$): δ=0.97-1.01 (m, 2H), 1.12-1.15 (m, 2H), 2.19 (m, 1H), 2.47 (s, 6H), 4.71 (s, 2H), 6.61 (s, 2H); LRMS: APCI$^-$: 230 [MH$^+$]

Preparation 35: 4-{[(E/Z)-1-(Cyclopropylcarbonyl)-2-(dimethylamino)vinyl]oxy}-2,6-dimethylbenzonitrile

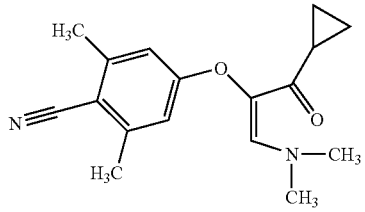

The benzonitrile of Preparation 34 (11.8 g, 51.46 mmol) and N,N-dimethylformamide dimethyl acetal (13.7 ml, 102.93 mmol) were heated at 105° C. for 12 hours. The reaction mixture was then concentrated under reduced pressure. The crude product was purified by flash chromatography on silica gel eluting with dichloromethane:pentane (50:50 then 80:20 then 100:0, by volume) to provide the title compound (11.19 g, 76%) as a white solid. $^1$H-NMR (400 MHz, CDCl$_3$): δ=0.63 (brs, 2H), 0.91 (brs, 2H), 1.93 (m, 1H), 2.44 (s, 6H), 2.96 (s, 6H), 6.69 (s, 2H); LRMS: APCI$^+$: 285 [MH$^+$].

Preparation 36: 4-[(3-Cyclopropyl-1H-pyrazol-4-yl)oxy]-2,6-dimethylbenzonitrile

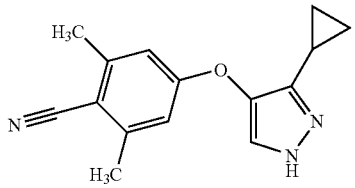

The benzonitrile of Preparation 35 (11.19 g, 39.3 mmol) was dissolved in acetic acid (62 ml). Hydrazine hydrate (2.11 ml, 43.6 mmol) was added, and the mixture was stirred at room temperature for 12 hours, under nitrogen. The reaction mixture was concentrated under reduced pressure, and the residue was partitioned between water (150 ml) and diethyl ether (200 ml). The organic layer was dried over magnesium sulphate, filtered and concentrated under reduced pressure to provide the title compound (9.71 g, 98%) as a solid. $^1$H-NMR (400 MHz, CDCl$_3$): δ=0.82-0.88 (m, 4H), 1.73 (m, 1H), 2.47 (s, 6H), 6.70 (s, 2H), 7.41 (s, 1H), 10.5 (brs, 1H); LRMS: APCl$^+$: m/z 254 [MH$^+$]; APCl$^-$: m/z 252 [M–H]$^-$.

Preparation 37: 4-[(3-Cyclopropyl-1-tetrahydro-2H-pyran-2-yl-1H-pyrazol-4-yl)oxy]-2,6-dimethylbenzonitrile

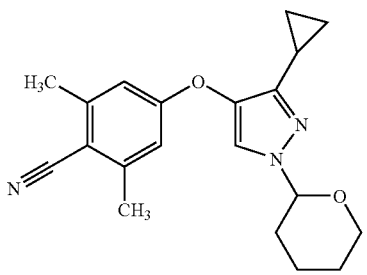

p-Toluenesulphonic acid (20 mg, 0.12 mmol) was added to a solution of the benzonitrile of Preparation 36 (1 g, 3.94 mmol) in tetrahydrofuran (30 ml). 3,4-Dihydro-2H-pyran (664 mg, 7.9 mmol) was then added dropwise at room temperature. The reaction mixture was stirred at room temperature, under nitrogen, for 15 hours. It was then evaporated under reduced pressure and the residue was partitioned between ethyl acetate (100 ml) and aqueous sodium bicarbonate (100 ml). The organic layer was washed with brine (50 ml), dried over sodium sulphate, filtered and concentrated under reduced pressure to provide the title compound (1.33 g, 100%). $^1$H-NMR (400 MHz, CDCl$_3$): δ=0.74-0.79 (m, 2H), 0.83-0.87 (m, 2H), 1.54-1.76 (m, 5H), 1.85 (m, 1H), 2.47 (s,6H), 3.51 (m, 1H), 3.68 (m, 1H), 3.88 (m, 1H), 4.09 (m, 1H), 6.70 (s, 2H), 7.40 (s, 1H), contaminated with some 3,4-dihydro-2H-pyran; LRMS: APCl$^+$: m/z 338 [MH$^+$] and m/z 254 [M-THP].

Preparations 38 & 39: 4-[(5-Chloro-3-cyclopropyl-1-tetrahydro-2H-pyran-2-yl-1H-pyrazol-4-yl)oxy]-2,6-dimethylbenzonitrile & 4-[(5-chloro-3-cyclopropyl-1H-pyrazol-4-yl) oxy]-2,6-dimethylbenzonitrile

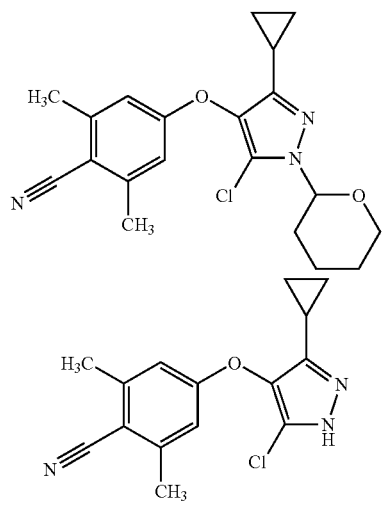

N-Chlorosuccinimide (764 mg, 5.71 mmol) was added to a solution of the pyrazole of Preparation 37 (1.33 g, 3.9 mmol) in N,N-dimethylformamide (30 ml). The reaction mixture was then heated at 50° C. for 15 hours. It was then evaporated under reduced pressure, and the residue was partitioned between dichloromethane (50 ml) and water (50 ml). The organic layers were dried over sodium sulphate, filtered, and then concentrated under reduced pressure. The crude product was purified by flash chromatography on silica gel eluting with ethyl acetate:pentane (gradient from 2:98 to 30:70, by volume) to provide the compound of Preparation 38 (388 mg, 18%) eluted first. $^1$H-NMR (400 MHz, CDCl$_3$): δ=0.65 (m, 1H), 0.84-0.92 (m, 3H), 1.60-1.63 (m, 2H), 1.68-1.73 (m, 3H), 1.94 (m, 1H), 2.14 (m, 1H), 2.48 (s, 7H), 3.67 (t, 1H), 5.50 (d, 1H), 6.62 (s, 2H); LRMS: APCl$^+$: m/z 288 [(M-THP)H$^-$].

Further elution provided the compound of Preparation 39 (325 mg, 20%). $^1$H-NMR (400 MHz, CDCl$_3$): δ=0.80-0.82 (m, 2H), 0.86-0.94 (m, 2H), 1.74 (m, 1H), 2.49 (s, 6H), 6.65 (s, 2H); LRMS: APCl$^+$: m/z 288 [MH$^+$]; APCl$^-$: m/z 286 [M–H].

Preparation 40: 4-(3,5-Dicyclopropyl-1-hydroxymethyl-1H-pyrazol-4-yloxy)-benzonitrile

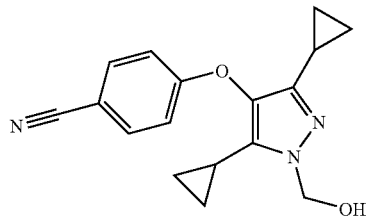

A mixture of the pyrazole from Preparation 9 (2.9 g, 10.9 mmol) and aqueous formaldehyde (37 wt % solution in water, 40 ml) was heated to 60° C. for 4 hours. The mixture was cooled and partitioned between ethyl acetate (100 ml) and saturated aqueous ammonium chloride (50 ml), and the layers were separated. The organic layer was washed with saturated aqueous ammonium chloride (3×30 ml) and then brine (30 ml), dried over magnesium sulphate, filtered and concentrated under reduced pressure to give crude title compound as a semi-solid (4.6 g, >100% due to impurities). $^1$H-NMR (400 MHz, CDCl$_3$): δ=0.78-0.82 (m, 8H), 1.6 (m, 2H), 5.55 (s, 2H), 7.0 (d, 2H), 7.6 (d, 2H); LRMS: APCl$^+$: m/z 296 [MH$^+$].

Preparation 41: 4-(1-Chloromethyl-3,5-dicyclopropyl-1H-pyrazol-4-yloxy)-benzonitrile

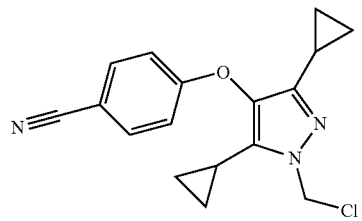

Thionyl chloride (1.14 ml, 15.2 mmol) was added to a solution of the crude hydroxymethyl pyrazole from Preparation 40 (approximately 10.9 mmol crude) in dichloromethane (50 ml). The mixture was stirred at room temperature for 24 hours and then another portion of thionyl chloride (1.14 ml, 15.2 mmol) was added and stirring was continued for an additional 90 minutes. The mixture was evaporated under reduced pressure and azeotroped with toluene (5×30 ml) to give crude title compound as a solid (3.8 g). $^1$H-NMR (400 MHz, CDCl$_3$): δ=0.78-0.82 (m, 8H), 1.55 (m, 1H), 1.60 (m, 1H), 5.9 (s, 2H), 7.0 (d, 2H), 7.6 (d, 2H).

Preparation 42: 4-Hydroxy-2-methyl benzonitrile

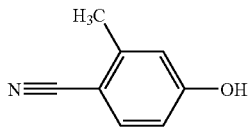

Boron trichloride (1M in dichloromethane, 747 ml, 747 mmol) was added dropwise, at −78° C., to a suspension of commercially available 4-methoxy-2-methyl-benzonitrile (44 g, 298 mmol) and tetrabutylammonium iodide (121 g, 327 mmol) in dichloromethane (750 ml), under nitrogen, over 40 minutes. Once the addition was complete, the yellow solution was warmed to room temperature and stirred for 16 hours at room temperature. The reaction mixture was then quenched by dropwise addition of water maintaining the internal temperature below 10° C. The mixture was filtered through Arbocel™ and the layers were separated. The aqueous layers were extracted again with dichloromethane (250 ml). The organic layers were combined, washed with a sodium thiosulphate solution (150 ml), dried over magnesium sulphate, filtered and concentrated under reduced pressure to give thick yellow oil. Trituration of the oil in dichloromethane, followed by filtration, provided a first crop of the title compound (10.8 g, 27%) as a white solid. The filtrate was evaporated and purified by flash chromatography on silica gel, eluting with pentane:ethyl acetate (70:30, by volume) to provide more of the title compound as a white solid (14.4 g, 36%). $^1$H-NMR (400 MHz, CDCl$_3$): δ=2.46 (s, 3H), 6.68 (d, 1H), 6.72 (s, 1H), 7.45 (d, 1H); LRMS: APCl$^-$: m/z 132 [M−H]$^-$.

Preparation 43: Trifluoromethanesulphonic acid 5-methoxy-quinolin-8-yl ester

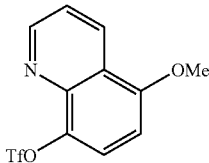

Trifluoromethanesulphonic anhydride (12 ml, 77.0 mmol) was added slowly, over approximately 5 minutes, to a stirred solution of 5-methoxy-quinolin-8-ol (Syn. Comm. 1997, 27(20), 3573-3579) (1.5 g, 8.6 mmol) and pyridine (5.5 ml, 68.5 mmol) in dichloromethane (34 ml) at 0° C., under nitrogen. The resulting mixture was allowed to warm to room temperature and stirred for a further 16 hours. The mixture was then partitioned between dichloromethane (100 ml) and saturated aqueous ammonium chloride solution (100 ml). The organic extract was further washed with water (100 ml), dried over magnesium sulphate, filtered and concentrated under reduced pressure to provide a crude yellow solid. Purification by flash chromatography on silica gel, eluting with 5% ethyl acetate, 95% pentane, provided the title compound as a pale yellow solid (2.62 g, 99%). $^1$H-NMR (400 MHz, CDCl$_3$): δ=4.02 (s, 3 H) 6.79 (d, 1 H) 7.50 (m, 2 H) 8.58 (dd, 1 H) 9.03 (dd, 1 H); LRMS: APCl$^+$: m/z 308 [MH$^+$].

Preparation 44: 5-Methoxy-quinoline-8-carbonitrile

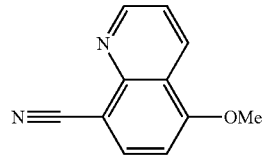

Sodium cyanide (835 mg, 17.0 mmol), tetrakis(triphenylphosphine)palladium (492 mg, 0.42 mmol), copper (I) iodide (162 mg, 0.85 mmol) and the product from Preparation 43 (2.62 g, 8.52 mmol) were mixed in a 250 ml round-bottomed flask and flushed with nitrogen. Acetonitrile (43 ml) was added and the resulting mixture was heated to reflux under nitrogen for 2 hours. The mixture was then diluted with ethyl acetate (200 ml) and filtered through Arbocel™. The filtrate was washed with water (100 ml), dried over magnesium sulphate, filtered and concentrated under reduced pressure. The crude product was purified by flash chromatography on silica gel eluting with ethyl acetate: pentane (gradient from 10:90 to 30:70, by volume) to provide the title compound as a pale yellow solid (1290 mg, 82%). $^1$H-NMR (400 MHz, CDCl$_3$): δ=4.08 (d, 3 H) 6.90 (d, 1 H) 7.51 (dd, 1 H) 8.06 (d, 1 H) 8.62 (dd, 1 H) 9.09 (dd, 1 H); LRMS: APCl$^+$: m/z 185 [MH$^+$].

Preparation 45: 5-Hydroxy-quinoline-8-carbonitrile

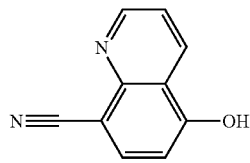

To a stirred solution of the carbonitrile from Preparation 44 (750 mg, 4.1 mmol) in 1-methyl pyrrolidinone (20 ml), at room temperature, under nitrogen, was added sodium thiophenolate (673 mg, 6.1 mmol) in one portion. The resulting mixture was heated to 200° C. for 14 hours. The mixture was then partitioned between diethyl ether (100 ml) and 1N aqueous NaOH (50 ml). The aqueous phase was acidified with 1N HCl (~50 ml) and extracted with diethyl ether (2×50 ml), and the organic extract was dried over sodium sulphate, filtered and concentrated under reduced pressure to provide the title compound as a yellow solid (210 mg, 30%). $^1$H-NMR (400 MHz, d-6 acetone): δ=7.15 (d, 1 H), 7.63 (m, 1H) 8.11 (dd, 1 H) 8.70 (d, 1 H) 9.07 (m, 1 H) 9.09 (dd, 1 H); LRMS: APCl$^+$: m/z 171 [MH$^-$].

EXAMPLE 1

4-(3,5-Dicyclopropyl-1-methanesulfonylmethyl-1H-pyrazol-4-yloxy)-benzonitrile

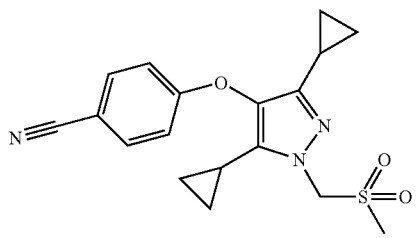

Step 1:

The pyrazole from Preparation 9 (10 g, 37.7 mmol) was dissolved in dimethoxyethane (200 ml). To this solution was added potassium tert-butoxide (4.65 g, 42 mmol) and then the mixture was warmed to 60° C. for 30 mins. Chloromethyl-methylsulphide (4 g, 42 mmol) was added and the reaction temperature was maintained at 60° C. for 2 hours. TLC indicated incomplete reaction so further portions of potassium tert-butoxide (2 g, 18 mmol) and chloromethyl-methylsulphide (2 g, 21 mmol) were added. After a further 90 minutes the reaction was cooled and partitioned between diethyl ether (500 ml) and 2N aqueous sodium hydroxide (200 ml). The layers were separated and the aqueous layer was extracted with diethyl ether (100 ml). The organic extracts were combined and washed with brine (100 ml), dried over magnesium sulphate, filtered and evaporated to give a yellow oil of the crude intermediate (4-(3,5-dicyclopropyl-1-methylsulfanylmethyl-1H-pyrazol-4-yloxy)-benzonitrile), which may be optionally purified by chromatography on silica gel eluting with ethyl acetate:pentane mixtures or taken on to Step 2 as crude sulphide.

Step 2:

Oxone® (30 g, 49 mmol) was added to a solution of the intermediate from Step 1 in methanol (500 ml) and water (40 ml). The reaction mixture was stirred at 60° C. for 18 hours and a further portion of Oxone® (10 g, 16 mmol) was added. After an additional 2 hours at 60° C. the mixture was partitioned between diethyl ether (800 ml) and 1N aqueous sodium hydroxide (300 ml). The layers were separated and the aqueous layer was extracted twice with diethyl ether (2×100 ml). The organic extracts were combined and washed with brine (100 ml), dried over magnesium sulphate, filtered and evaporated to give a yellow solid. The solid was purified by chromatography on silica gel eluting with ethyl acetate:pentane (1:1) to give the title compound (7.4 g). This solid was crystallised from ethanol to give pure title compound (5.4 g, 40%) $^1$H-NMR (400 MHz, CDCl$_3$): δ=0.71 (m, 2H), 0.78-0.85 (m, 6H), 1.58 (m, 1H), 1.72 (m, 1H), 3.03 (s, 3H), 5.26 (s, 2H), 6.99 (d, 2H), 7.61 (d, 2H); LRMS: APCl$^+$: m/z 358 [MH$^+$]; mpt. 141.5-142.5° C.

EXAMPLES: 2 TO 16

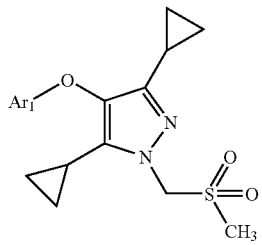

Compounds of the general formula above were prepared by a using a method similar to Example 1 using the pyrazoles from Preparations 10 to 24.

| Ex No | Ar$_1$- | Analytical Data |
|---|---|---|
| 2 | ![H3C-phenyl-CN] | $^1$H-NMR(400 MHz, CDCl$_3$): δ= 0.69-0.72(m, 2H), 0.78-0.81(m, 4H), 0.85-0.87(m, 2H), 1.58(m, 1H), 1.72(m, 1H), 2.52(s, 3H), 3.02(s, 3H), 5.25(s, 2H), 6.76(d, 1H), 6.86(s, 1H), 7.54(d, 1H); LRMS: APCl$^+$: m/z 372[MH$^+$]; Mp = 140.7 to 141.3° C.; (72% yield) |

-continued

| Ex No | Ar₁- | Analytical Data |
|---|---|---|
| 3 | 2,6-dimethyl-4-substituted benzonitrile (H₃C and CH₃ substituents on ring with CN) | ¹H-NMR(400 MHz, CDCl₃): δ= 0.69-0.73(m, 2H), 0.78-0.81(m, 4H), 0.83-0.88(m, 2H), 1.58(m, 1H), 1.71(m, 1H), 2.48(s, 6H), 3.02(s, 3H), 5.26(s, 2H), 6.64(s, 2H); LRMS: APCl⁺: m/z 386 [MH⁺]; (75% yield) |
| 4 | 3-chloro-4-substituted benzonitrile | ¹H-NMR(400 MHz, CDCl₃): δ= 0.69-0.72(m, 2H), 0.78-0.83(m, 4H), 0.87-0.90(m, 2H), 1.56(m, 1H), 1.72(m, 1H), 3.03(s, 3H), 5.25(s, 2H), 6.89(d, 1H), 7.07(s, 1H), 7.61(d, 1H); LRMS: APCl⁺: m/z 392[MH⁺]; (85% yield) |
| 5 | 3-fluoro-4-substituted benzonitrile | ¹H-NMR(400 MHz, CDCl₃): δ= 0.71(m, 2H), 0.79-0.89(m, 6H), 1.57(m, 1H), 1.72(m, 1H), 3.03(s, 3H), 5.25(s, 2H), 6.79(m, 2H), 7.56(m, 1H); LRMS: APCl⁺: m/z 376[MH⁺]; (88% yield) |
| 6 | 3-chloro-4-substituted benzonitrile (isomer) | ¹H-NMR(400 MHz, CDCl₃): δ= 0.81(m, 4H) 1.60(m, 1H) 1.71(m, 1H) 3.03(s, 1H)5.26(s, 1H)6.82(d, 1H) 7.49(dd, 1H) 7.74(d, 1H); LRMS: APCl⁺: m/z 392[MH⁺]; (75% yield) |
| 7 | 3-fluoro-4-substituted benzonitrile (isomer) | ¹H-NMR(400 MHz, CDCl₃): δ= 0.72-0.89(m, 3H), 1.61(m, 1H), 1.71(m, 1H), 3.02(s, 3H), 5.25(s, 2H), 6.86(t, 1H), 7.38(m, 1H), 7.46(dd, 1H); LRMS: APCl⁺: m/z 376[MH⁺]; (85% yield) |
| 8 | 3-methoxy-4-substituted benzonitrile | ¹H-NMR(400 MHz, CDCl₃): δ= 0.72-0.85(m, 8H), 1.59(m, 1H), 173(s, 1H), 3.00(s, 3H), 3.98(s, 3H), 5.25(s, 2H), 6.72(d, 1H), 7.20(m, 2H); LRMS: APCl⁺: m/z 388 [MH⁺]; (70% yield) |
| 9 | 4-cyanonaphthalen-1-yl | ¹H-NMR(400 MHz, CDCl₃): δ= 0.65-0.74(m, 8H), 1.51(m, 1H), 1.70(m, 1H), 2.99(s, 3H), 5.22(s, 2H), 6.63(d, 1H), 7.64(m, 1H), 7.71(m, 2H), 8.18(d, 1H), 8.42(d, 1H); LRMS: APCl⁺: m/z 408[MH⁺]; (90% yield) |
| 10 | 8-cyanoquinolin-5-yl | ¹H-NMR(400 MHz, CDCl₃): δ= 0.72-0.77(m, 8H), 1.50(m, 1H), 1.71(s, 1H), 3.00(s, 3H), 5.23(s, 2H), 6.71(d, 1H), 7.56(dd, 1H), 7.96(d, 1H), 8.72(dd, 1H), 9.11(dd, 1H); LRMS: APCl⁺: m/z 409[MH⁺]; (85% yield) |

-continued

| Ex No | Ar₁- | Analytical Data |
|---|---|---|
| 11 | 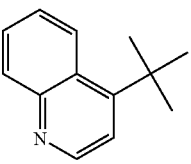 | ¹H-NMR(400 MHz, CDCl₃): δ= 0.69-0.87(m, 8H), 1.58(m, 1H), 1.76(m, 1H), 3.03(s, 3H), 5.27(s, 2H), 6.61(d, 1H), 7.63(t, 1H), 7.80(m, 1H), 8.19(d, 1H), 8.37(d, 1H), 8.72(d, 1H); LRMS: APCI⁺: m/z 384[MH⁺]; (69% yield) |
| 12 | 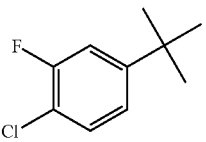 | ¹H-NMR(400 MHz, CDCl₃): δ= 0.65-0.74(m, 8H) 1.59(m, 1H) 1.73(m, 1H) 3.02(s, 3H) 5.25(s, 2H) 6.64(m, 1H), 6.75(m, 1H), 7.30(m, 1H); LRMS: APCI⁺: m/z 385/387[MH⁺]; (80% yield) |
| 13 | 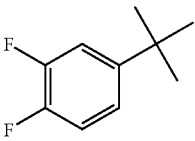 | ¹H-NMR(400 MHz, CDCl₃): δ= 0.65-0.74(m, 8H) 1.59(m, 1H) 1.73(m, 1H) 3.02(s, 3H) 5.25(s, 2H) 6.60(m, 1H), 6.76(m, 1H), 7.08(m, 1H); LRMS: APCI⁺: m/z 369[MH⁺]; (75% yield) |
| 14 | 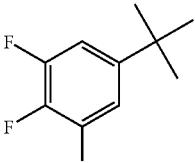 | ¹H-NMR(400 MHz, CDCl₃): δ= 0.73(m, 2H), 0.81(m, 2H), 0.88 (m, 2H), 1.13(d, 2H), 1.59(m, 1H), 1.73(m, 1H), 3.02(s, 3H), 5.25(s, 2H), 6.55(dd, 2H); LRMS: APCI⁺: m/z 387[MH⁺]; (50% yield) |
| 15 | 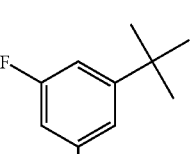 | ¹H-NMR(400 MHz, CDCl₃): δ= 0.65-0.74(m, 8H), 1.59(m, 1H), 1.73(m, 1H), 3.02(s, 3H), 5.25(s, 2H), 6.40-6.55(m, 3H); LRMS: APCI⁺: m/z 369[MH⁺]; (77% yield) |
| 16 | 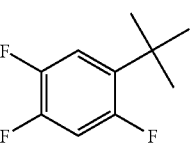 | ¹H-NMR(400 MHz, CDCl₃): δ= 0.65-0.74(m, 8H), 1.59(m, 1H), 1.73(m, 1H), 3.02(s, 3H), 5.25(s, 2H), 6.65(m, 1H), 7.04(m, 1H); LRMS: APCI⁺: m/z 387[MH⁺]; (78% yield) |

EXAMPLES: 17 TO 20

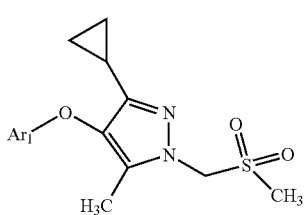

regioisomer 1

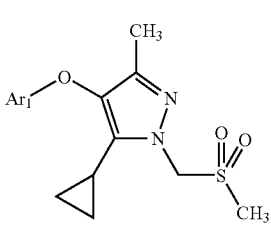

regioisomer 2

Compounds of the general formulae above were prepared by a method similar to Example 1 using the pyrazoles from Preparations 25 to 26. The regioisomers were separated using chromatography in silica gel with regioisomer 1 eluting before regioisomer 2.

| Ex No | Ar$_1$- | Analytical Data |
|---|---|---|
| 17, 18 | 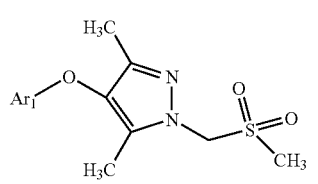 | Regioisomer 1: $^1$H-NMR(400 MHz, CDCl$_3$): δ= 0.78-0.82(m, 4H), 1.60(m, 1H), 2.18(s, 3H), 2.51(s, 3H), 2.97(s, 3H), 5.11 (s, 2H), 6.76(d, 1H), 6.84(s, 1H), 7.53(d, 1H); LRMS: APCl$^+$: m/z 346[MH$^+$]; (35% yield)<br>Regioisomer 2: $^1$H-NMR(400 MHz, CDCl$_3$): δ= 0.70-0.73(m, 2H), 0.85-0.89(m, 2H), 1.73(m, 1H), 2.03(s, 3H), 2.51(s, 3H), 3.06(s, 3H), 5.30(s, 2H), 6.72(d, 1H), 6.81(s, 1H), 7.53(d, 1H); LRMS: APCl$^+$: m/z 346[MH$^+$]; (25% yield) |
| 19, 20 | 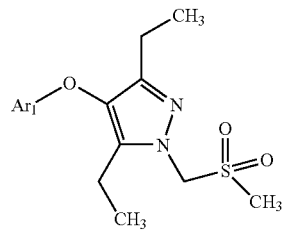 | Regioisomer 1: $^1$H-NMR(400 MHz, CDCl$_3$) : δ = 0.80-0.83(m, 4H), 1.63(m, 1H), 2.17(s, 3H), 2.48(s, 6H), 2.97(s, 3H), 5.12 (s, 2H), 6.63(s, 2H); LRMS: APCl$^+$: m/z 360[MH$^+$]. (30% yield)<br>Regioisomer 2: $^1$H-NMR(400 MHz, CDCl$_3$): δ= 0.71-0.73(m, 2H), 0.85-0.88(m, 2H), 1.75(m, 1H), 2.01(s, 3H), 2.47(s, 6H), 3.05(s, 3H), 5.29(s, 2H), 6.59(s, 2H); LRMS: APCl$^+$: m/z 360 [MH$^+$]. (22% yield) |

EXAMPLE: 21    EXAMPLES: 22 TO 23

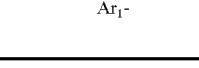

Compounds of the general formula above were prepared by a method similar to Example 1 using the pyrazole from Preparation 27.

Compounds of the general formula above were prepared by a method similar to Example 1 using the pyrazoles from Preparations 28 to 29.

| Ex No | Ar$_1$- | Analytical Data |
|---|---|---|
| 21 | H$_3$C, N, CH$_3$ substituted phenyl | $^1$H-NMR(400 MHz, CDCl$_3$): δ= 2.06(s, 3H), 2.20(s, 3H), 2.48(s, 6H), 3.00(s, 3H), 5.15(s, 2H), 6.60(s, 2H); LRMS: APCl$^+$: m/z 334[MH$^+$]. (86% yield) |

| Ex No | Ar₁- | Analytical Data |
|---|---|---|
| 22 | 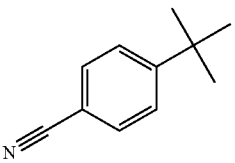 | $^1$H-NMR(400 MHz, CDCl$_3$): δ= 1.12(t, 6H), 2.40(q, 2H), 2.64 (q, 2H), 3.02(s, 3H), 5.17(s, 2H), 6.96(d, 2H), 7.60(d, 2H); LRMS: APCl$^+$: m/z 334[MH$^+$]. (88% yield) |
| 23 | 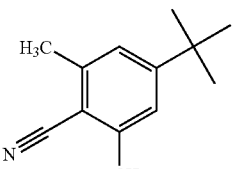 | $^1$H-NMR(400 MHz, CDCl$_3$): δ= 1.13(t, 6H), 2.41(q, 2H), 2.47(s, 6H), 2.64(q, 2H), 3.01(s, 3H), 5.17(s, 2H), 6.61(s, 2H); LRMS: APCl$^+$: m/z 362[MH$^+$]; (90% yield) |

EXAMPLES: 24 TO 26

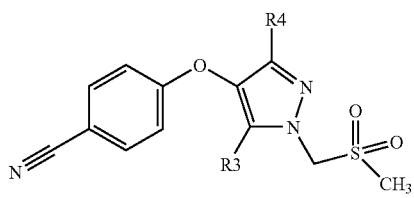

Compounds of the general formula above were prepared by a method similar to Example 1 using the pyrazoles from Preparations 30 to 31. Regioisomers 25 and 26 were separated by chromatography with 25 eluting before 26.

| Ex No | R3, R4 | Analytical Data |
|---|---|---|
| 24 | tBu, tBu | $^1$H-NMR(400MHz, CDCl$_3$): δ=1.15(s, 9H), 1.3(s, 9H), 3.2(s, 3H), 5.4(s, 2H). 6.96(d, 2H), 7.60(d, 2H); LRMS: APCl$^+$: m/z 390[MH$^+$]. (50% yield). |
| 25 | Me, tBu | $^1$H-NMR(400MHz, CDCl$_3$): δ=1.2(s, 9H), 2.1(s, 3H), 3.0(s, 3H), 5.15(s, 2H), 6.96(d, 2H), 7.60(d, 2H); LRMS: APCl$^+$: m/z 348[MH$^+$]. (10% yield). |
| 26 | tBu, Me | $^1$H-NMR(400MHz, CDCl$_3$): δ=1.4(s, 9H), 1.95(s, 3H), 3.15(s, 3H), 5.4(s, 2H), 6.96(d, 2H), 7.60(d, 2H); LRMS: APCl$^+$: m/z 348[MH$^+$]. (5% yield) |

EXAMPLES 27 & 28

4-(3-Chloro-5-cyclopropyl-1-methanesulfonylmethyl-1H-pyrazol-4-yloxy)-2,6-dimethyl-benzonitrile & 4-(5-Chloro-3-cyclopropyl-1-methanesulfonylmethyl-1H-pyrazol-4-yloxy)-2,6-dimethyl-benzonitrile

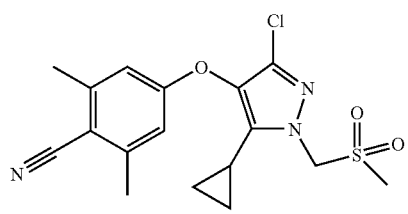

-continued

Examples 27 and 28 were prepared by a method similar to Example 1 using the pyrazole from Preparation 39, but the regioisomers were isolated as a 40:60 mixture. $^1$H-NMR (400 MHz, CDCl$_3$): δ=0.78-0.80 (m, 2H, major regioisomer A), 0.84-0.88 (m, 4H, minor regioisomer B), 0.93-0.96 (m, 2H, A), 1.69 (m, 1H, A), 1.79 (m, 1H, B), 2.50 (s, 6H, A+B), 3.04 (s, 3H, B), 3.10 (s, 3H, A), 5.19 (s, 2H, B), 5.31 (s, 2H, A), 6.62 (s, 2H, A), 6.67 (s, 2H, B); LRMS: APCl$^+$: m/z 380 [MH$^+$].

EXAMPLES: 29 & 30

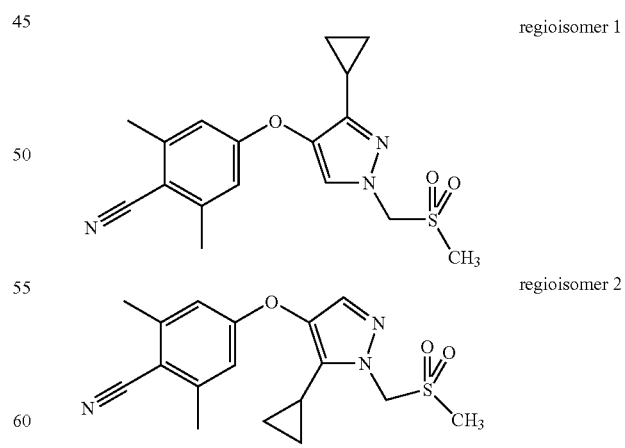

Compounds of the general formula above were prepared by a method similar to Example 1 using the pyrazole from Preparations 36. The regioisomers were separated using chromatography in silica gel with regioisomer 1 eluting before regioisomer 2.

| Ex No | Analytical Data |
|---|---|
| 29 | Regioisomer 1: $^1$H-NMR (400 MHz, CDCl$_3$): δ = 0.85 (m, 4 H) 1.66 (m, 1 H) 2.48 (s, 6 H) 2.90 (s, 3 H) 5.13 (s, 2 H) 6.70 (s, 2 H) 7.48 (s, 1 H); LRMS APCl$^+$ : m/z 346 [MH$^+$]; (32% yield) |
| 30 | Regioisomer 2: 1H-NMR (400 MHz, CDCl3): δ = 0.75 (m, 2 H) 0.91 (m, 2 H) 1.77 (m, 1 H) 2.48 (m, 6 H) 3.05 (s, 3 H) 5.36 (s, 2 H) 6.65 (s, 2 H) 7.39 (s, 1 H); LRMS : APCl$^+$ : m/z 346 [MH$^+$]; (4% yield) |

EXAMPLE 31

4-({3,5-Diethyl-1-[(methylsulfonyl)methyl]-1H-pyrazol-4-yl}methyl)benzonitrile

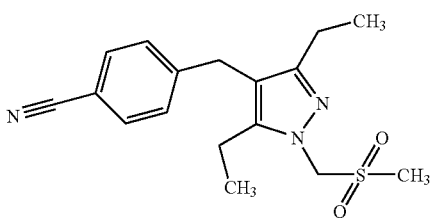

The title compound (123 mg, 87%) was prepared by a similar method to that of Example 1 using the pyrazole of Preparation 33. $^1$H-NMR (400 MHZ, CDCl$_3$): δ=1.04-1.12 (M, 6H), 2.40 (Q, 2H), 2.67 (Q, 2H), 3.00 (S, 3H), 3.82 (S, 2H), 5.20 (S, 2H), 7.19 (D, 2H), 7.56 (D, 2H); LRMS: APCl$^+$: M/Z 332 [MH$^+$].

EXAMPLE 32

4-(3,5-Dicyclopropyl-1-trifluoromethanesulfonylmethyl-1H-pyrazol-4-yloxy)-benzonitrile

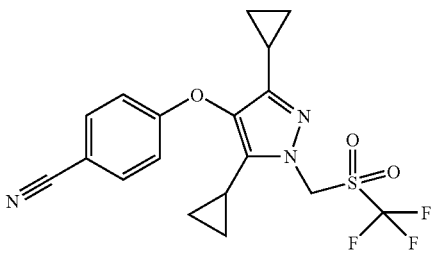

Step 1:

CuSCF$_3$ (0.21 g, 1.28 mmol) was added to a solution of the pyrazole of Preparation 41 (0.2 g, 0.64 mmol) in dimethylformamide (10 ml) and stirred for 3 days at room temperature. The mixture was diluted with water (30 ml) and extracted with ethyl acetate (2×20 ml). The combined organic extracts were washed with water (3×30 ml), dried over magnesium sulphate, filtered and concentrated under reduced pressure. The residue was purified by chromatography on silica gel eluting with ethyl acetate:pentane (10:90) to give the sulphide intermediate (75 mg, 31%). $^1$H-NMR (400 MHz, CDCl$_3$): δ=0.78-0.82 (m, 8H), 1.25 (m, 2H), 5.55 (s, 2H), 7.0 (d, 2H), 7.6 (d, 2H). LRMS APCl$^+$: m/z 380 [MH$^+$].

Step 2:

Oxone® (610 mg, 1 mmol) was added to a solution of the intermediate sulphide (75 mg) from Step 1 above in methanol (10 ml) and water (2 ml). The reaction mixture was stirred at room temperature for 18 hours and a further portion of Oxone® (244 mg, 0.2 mmol) was added. After an additional 24 hours, the mixture was partitioned between diethyl ether (30 ml) and water (30 ml). The layers were separated and the aqueous layer was extracted twice with diethyl ether (2×10 ml). The organic extracts were combined and washed with brine (10 ml), dried over magnesium sulphate, filtered and evaporated to give a brown residue. The residue was purified by chromatography on silica gel eluting with a gradient of 5-10% dichloromethane in pentane to give the title compound (16 mg, 20%). $^1$H-NMR (400 MHz, CDCl$_3$): δ=0.65-0.90 (m, 8H), 1.55 (m, 1H), 1.65 (m, 1H), 5.4 (s, 2H), 6.99 (d, 2H), 7.6 (d, 2H); LRMS: APCl$^+$: m/z 412 [MH$^+$].

EXAMPLE 33

4-(3,5-Dicyclopropyl-1-ethanesulfonylmethyl-1H-pyrazol-4-yloxy)-benzonitrile

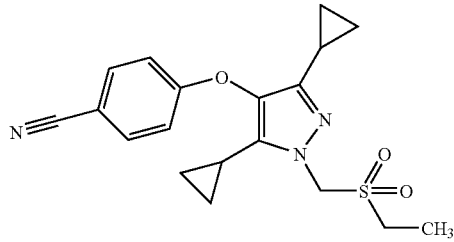

Step 1:

Sodium ethylthiolate (54 mg, 0.64 mmol) was added to a solution of the chloromethyl pyrazole of Preparation 41 (0.2 g, 0.64 mmol) in 1,4-dioxane (5 ml) and stirred for 18 hours at room temperature. The mixture was diluted with water (30 ml) and extracted with diethyl ether (2×20 ml). The combined organic extracts were washed with water (3×30 ml), dried over magnesium sulphate, filtered and concentrated under reduced pressure. The residue was purified by chromatography on silica gel eluting with ethyl acetate:pentane (10:90) to give the sulphide intermediate as a solid (135 mg, 70%). $^1$H-NMR (400 MHz, CDCl$_3$): δ=0.65-0.82 (m, 8H), 1.2 (t, 3H), 1.5 (m, 1H), 1.6 (m, 1H), 2.65 (q, 2H), 5.15 (s, 2H), 7.0 (d, 2H), 7.6 (d, 2H).LRMS: APCl$^+$: m/z 340 [MH$^+$].

Step 2:

Oxone® (732 mg, 12 mmol) was added to a solution of the intermediate sulphide (135 mg) from Step 1 above in methanol (10 ml) and water (2 ml). The reaction mixture was stirred at room temperature for 18 hours and partitioned between diethyl ether (30 ml) and water (30 ml). The layers were separated and the aqueous layer was extracted twice with diethyl ether (2×10 ml). The organic extracts were combined and washed with brine (10 ml), dried over magnesium sulphate, filtered and evaporated to give a solid residue. The residue was purified by chromatography on silica gel eluting with a gradient of 5-10% dichloromethane in pentane to give the title compound as a colourless solid (59 mg, 40%). ¹H-NMR (400 MHz, CDCl₃): δ=0.7-0.9 (m, 8H), 1.4 (t, 3H), 1.55 (m, 1H), 1.7 (m, 1H), 3.1 (q, 2H), 5.20 (s, 2H), 7.0 (d, 2H), 7.6 (d, 2H).LRMS: APCI⁺: m/z 372 [MH⁺].

EXAMPLES: 34 & 35

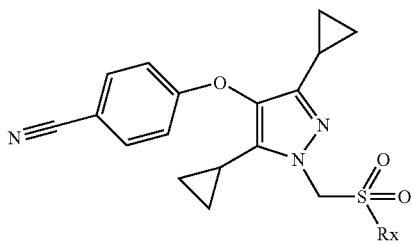

Compounds of the general formula above were prepared by a method similar to Example 33 using the appropriate sodium alkylthiolate, followed by oxidation with Oxone®.

| Ex No | Rx- | Analytical Data |
|---|---|---|
| 34 | —CH(CH₃)₂ | ¹H-NMR(400MHz, CDCl₃): δ=0.7-0.9(m, 8H), 1.4(d, 6H), 1.55 (m, 1H), 1.8(m, 1H), 3.35(m, 2H), 5.30(s, 2H), 7.0(d, 2H), 7.6 (d, 2H); LRMS: APCI⁺:m/z 386 [MH⁺]. (31% yield overall) |
| 35 | —C(CH₃)₃ | ¹H-NMR(400MHz, CDCl₃): δ=0.70(m, 2H), 0.79(m, 4H), 0.87(m, 2H), 1,45(s, 9H), 1.56(m, 1H), 1.90(m, 1H), 5.39(s, 2H) 6.96(d, 2H), 7.6(d, 1H); LRMS(electrospray): m/z 422[MNa⁺]. (29% yield overall) |

EXAMPLE 36

4-(1-Benzenesulfonylmethyl-3,5-dicyclopropyl-1H-pyrazol-4-yloxy)-benzonitrile

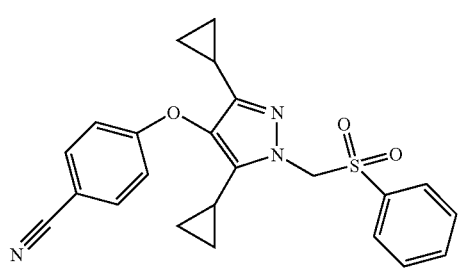

The title compound (275 mg, 66% yield) was prepared by a similar method to that of Example 1 using the pyrazole from Preparation 9 (265 mg, 1 mmol) and chloromethyl phenyl sulphide in place of chloromethyl methyl sulphide in Step 1, followed by oxidation using Oxone®, by a similar method to Step 2. ¹H-NMR (400 MHz, CDCl₃): δ=0.45 (m, 2H), 0.60-0.70 (m, 4H), 0.88 (m, 2H), 1.40 (m, 1H), 1.77 (m, 1H), 5.40 (s, 2H), 6.98 (d, 2H), 7.55 (m, 2H), 7.6 (d, 2H), 7.72 (m, 1H), 7.78 (m, 2H); RMS (electrospray): m/z 420 [MH⁺]. (66% yield overall). By controlling the equivalents of Oxone® in the oxidation of sulphide to sulphone it is possible to isolate the sulphoxide intermediate. This is illustrated by the following Examples 37 and 38.

EXAMPLE 37

4-({3,5-Diethyl-1-[(methylsulfinyl)methyl]-1H-pyrazol-4-yl}oxy)-2,6-dimethylbenzonitrile

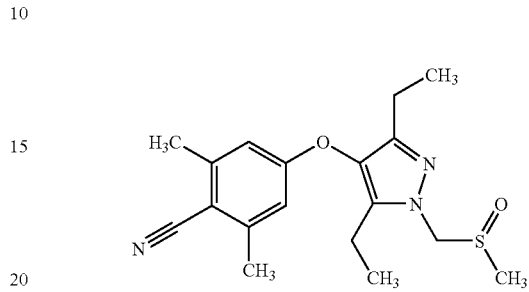

Oxone® (0.5 equivalents; 120 mg. 0.2 mmol)) was added to a solution of a portion of the sulphide formed after Step 1 of Example 23 (130 mg, 0.39 mmol) in methanol (10 ml) and water (2 ml). The reaction mixture was stirred at room temperature for 3 hours, after which time it was evaporated in vacuo and the residue was partitioned between water (10 ml) and dichloromethane (15 ml). The organic layers were dried over magnesium sulphate, filtered and then evaporated. The resulting crude product was purified by flash chromatography on silica gel eluting with ethyl acetate: pentane (1:1, by volume) to provide the title compound (100 mg, 73%). ¹H-NMR (400 MHz, CDCl₃): δ=1.09-1.14 (m, 6H), 2.40 (q, 2H), 2.46 (s, 6H), 2.62-2.66 (m, 5H), 5.02 (d, 1H), 5.16 (d, 1H), 6.61 (s, 2H); LRMS: APCI⁺: m/z 346 [MH⁺].

EXAMPLE 38

4-({3,5-Dimethyl-1-[(methylsulfinyl)methyl]-1H-pyrazol-4-yl}oxy)-2,6-dimethylbenzonitrile

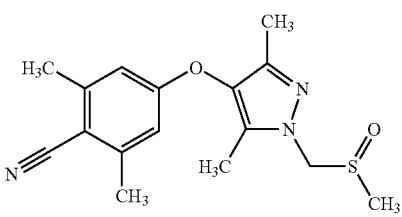

The title compound (145 mg, 63%) was prepared by a similar method to that of Example 37 using a portion of the sulphide formed after Step 1 of Example 21 and Oxone® (0.5 equivalent). ¹H-NMR (400 MHz, CDCl₃): δ=2.06 (s, 3H), 2.21 (s, 3H), 2.47 (s, 6H), 2.64 (s, 3H), 4.98 (d, 1H), 5.16 (d, 1H), 6.60 (s, 2H); LRMS: APCI⁺: m/z 318 [MH⁺].

EXAMPLE 39

Examples of specific compounds, tested in Screen 1.0 as described above for functional progesterone antagonism, are illustrated in the table below.

| Example No. | IC$_{50}$ (nM) |
| --- | --- |
| 3 | 8 |
| 5 | 44 |
| 17 | 22 |
| 19 | 7 |
| 20 | 15 |
| 23 | 6 |

The invention claimed is:
1. A compound of formula (I)

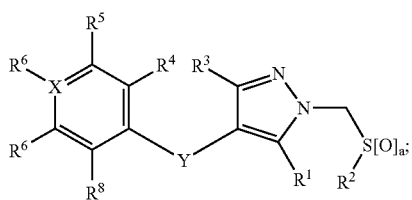

or a pharmaceutically acceptable salt thereof, wherein:
R$^1$ and R$^3$ independently represent H, C$_{1-6}$alkyl, C$_{3-8}$cycloalkyl, or halogen;
R$^2$ represents C$_{1-6}$alkyl, CF$_3$ or aryl;
a represents 1 or 2;
R$^4$, R$^5$, R$^7$ and R$^8$ independently represent H, C$_{1-6}$alkyl, C$_{1-6}$alkyloxy, CN or halogen, or R$^4$ and R$^5$, or R$^7$ and R$^8$, together with the ring to which they are attached form an aryl or heterocyclic fused ring system;
X represents C or N;
Y represents CH$_2$ or O; and
R$^6$ represents H, CN or halo provided that, when X represents N, R$^6$ is absent.

2. A compound according to claim 1, wherein R$^1$ represents C$_{1-6}$alkyl or C$_{3-8}$cycloalkyl.

3. A compound according to claim 1, wherein R$^2$ represents C$_{1-6}$alkyl.

4. A compound according to claim 1, wherein R$^3$ represents C$_{1-6}$alkyl or C$_{3-8}$cycloalkyl.

5. A compound according to claim 1, wherein R$^4$ represents H.

6. A compound according to claim 1, wherein R$^5$ represents H, C$_{1-6}$ alkyl, or halogen.

7. A compound according to claim 1, wherein R$^4$ and R$^5$ together represent a phenyl or pyridinyl ring fused to the ring to which they are attached.

8. A compound according to claim 1, wherein R$^6$ represents CN.

9. A compound according to claim 1, wherein R$^7$ represents H, C$_{1-6}$ alkyl, or halogen.

10. A compound according to claim 1, wherein R$^8$ represents H.

11. A compound according to claim 1, wherein Y represents O.

12. A compound according to claim 1, selected from the group consisting of:
   4-(3,5-dicyclopropyl-1-methanesulfonylmethyl-1H-pyrazol-4-yloxy)-benzonitrile;
   4-(3,5-dicyclopropyl-1-methanesulfonylmethyl-1H-pyrazol-4-yloxy)-2-methyl-benzonitrile;
   4-(3,5-dicyclopropyl-1-methanesulfonylmethyl-1H-pyrazol-4-yloxy)-2,6-dimethyl-benzonitrile;
   2-chloro-4-(3,5-dicyclopropyl-1-methanesulfonylmethyl-1H-pyrazol-4-yloxy)-benzonitrile;
   4-(3,5-dicyclopropyl-1-methanesulfonylmethyl-1H-pyrazol-4-yloxy)-2-fluoro-benzonitrile;
   3-chloro-4-(3,5-dicyclopropyl-1-methanesulfonylmethyl-1H-pyrazol-4-yloxy)-benzonitrile;
   4-(3,5-dicyclopropyl-1-methanesulfonylmethyl-1H-pyrazol-4-yloxy)-3-fluoro-benzonitrile;
   4-(3,5-dicyclopropyl-1-methanesulfonylmethyl-1H-pyrazol-4-yloxy)-3-methoxy-benzonitrile;
   4-(3,5-dicyclopropyl-1-methanesulfonylmethyl-1H-pyrazol-4-yloxy)-naphthalene-1-carbonitrile;
   5-(3,5-dicyclopropyl-1-methanesulfonylmethyl-1H-pyrazol-4-yloxy)-quinoline-8-carbonitrile;
   4-(3,5-dicyclopropyl-1-methanesulfonylmethyl-1H-pyrazol-4-yloxy)-quinoline;
   4-(4-chloro-3-fluoro-phenoxy)-3,5-dicyclopropyl-1-methanesulfonylmethyl-1H-pyrazole;
   3,5-dicyclopropyl-4-(3,4-difluoro-phenoxy)-1-methanesulfonylmethyl-1H-pyrazole;
   3,5-dicyclopropyl-1-methanesulfonylmethyl-4-(3,4,5-trifluoro-phenoxy)-1H-pyrazole;
   3,5-dicyclopropyl-4-(3,5-difluoro-phenoxy)-1-methanesulfonylmethyl-1H-pyrazole;
   3,5-dicyclopropyl-1-methanesulfonylmethyl-4-(2,4,5-trifluoro-phenoxy)-1H-pyrazole;
   4-(3-cyclopropyl-1-methanesulfonylmethyl-5-methyl-1H-pyrazol-4-yloxy)-2-methyl-benzonitrile;
   4-(5-cyclopropyl-1-methanesulfonylmethyl-3-methyl-1H-pyrazol-4-yloxy)-2-methyl-benzonitrile;
   4-(3-cyclopropyl-1-methanesulfonylmethyl-5-methyl-1H-pyrazol-4-yloxy)-2,6-dimethyl-benzonitrile;
   4-(5-cyclopropyl-1-methanesulfonylmethyl-3-methyl-1H-pyrazol-4-yloxy)-2,6-dimethyl-benzonitrile;
   4-(1-methanesulfonylmethyl-3,5-dimethyl-1H-pyrazol-4-yloxy)-2,6-dimethyl-benzonitrile;
   4-(3,5-diethyl-1-methanesulfonylmethyl-1H-pyrazol-4-yloxy)-benzonitrile;
   4-(3,5-diethyl-1-methanesulfonylmethyl-1H-pyrazol-4-yloxy)-2,6-dimethyl-benzonitrile;
   4-(3,5-di-tert-butyl-1-methanesulfonylmethyl-1H-pyrazol-4-yloxy)-benzonitrile;
   4-(3-tert-butyl-1-methanesulfonylmethyl-5-methyl-1H-pyrazol-4-yloxy)-benzonitrile;
   4-(5-tert-butyl-1-methanesulfonylmethyl-3-methyl-1H-pyrazol-4-yloxy)-benzonitrile;
   4-(3-chloro-5-cyclopropyl-1-methanesulfonylmethyl-1H-pyrazol-4-yloxy)-2,6-dimethyl-benzonitrile;
   4-(5-chloro-3-cyclopropyl-1-methanesulfonylmethyl-1H-pyrazol-4-yloxy)-2,6-dimethyl-benzonitrile;
   4-(3-cyclopropyl-1-methanesulfonylmethyl-1H-pyrazol-4-yloxy)-2,6-dimethyl-benzonitrile;
   4-(5-cyclopropyl-1-methanesulfonylmethyl-1H-pyrazol-4-yloxy)-2,6-dimethyl-benzonitrile;
   4-(3,5-diethyl-1-methanesulfonylmethyl-1H-pyrazol-4-ylmethyl)-benzonitrile;
   4-(3,5-dicyclopropyl-1-trifluoromethanesulfonylmethyl-1H-pyrazol-4-yloxy)-benzonitrile;
   4-(3,5-dicyclopropyl-1-ethanesulfonylmethyl-1H-pyrazol4-yloxy)-benzonitrile;
   4-[3,5-dicyclopropyl-1-(propane-2-sulfonylmethyl)-1H-pyrazol-4-yloxy]-benzonitrile;
   4-[3,5-dicyclopropyl-1-(2-methyl-propane-2-sulfonylmethyl)-1H-pyrazol-4-yloxy]-benzonitrile;
   4-(1-benzenesulfonylmethyl-3,5-dicyclopropyl-1H-pyrazol-4-yloxy)-benzonitrile;
   4-(3,5-diethyl-1-methanesulfinylmethyl-1H-pyrazol-4-yloxy)-2,6-dimethyl-benzonitrile; and 4-(3,5-diethyl-1-methanesulfinylmethyl-1H-pyrazol-4-yloxy)-2,6-dimethyl-benzonitrile;
or a pharmaceutically acceptable salt thereof.

13. A process for making a compound according to claim 1, wherein a represents 1, comprising oxidising a compound of formula (II)

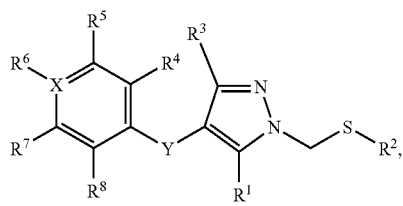

(II)

wherein $R^1$ to $R^8$, X and Y are as defined in claim 1.

14. A process for making a compound according to claim 1, wherein a represents 2, comprising oxidising a compound of formula (II)

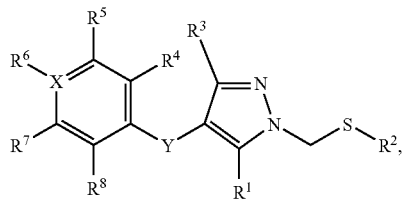

(II)

wherein $R^1$ to $R^8$, X and Y are as defined in claim 1.

15. A process for making a compound according to claim 1, wherein a represents 2, comprising oxidising a compound of formula (Ia)

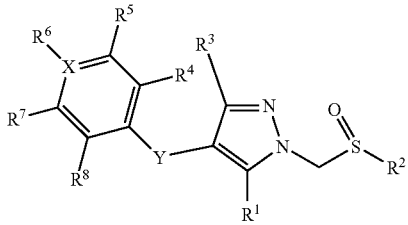

(Ia)

wherein $R^1$ to $R^8$, X and Y are as defined above.

16. A pharmaceutical formulation comprising a compound according to claim 1, or a pharmaceutically acceptable salt thereof, together with a pharmaceutically acceptable excipient, diluent or carrier.

17. A method of treatment of a mammal to treat endometriosis comprising treating said mammal with an effective amount of a compound according to claim 1, or with a pharmaceutically acceptable salt or composition thereof.

18. 4-(3Cyclopropyl-1-methanesulfonylmethyl-5-methyl-1H-pyrazol-4-yloxy)-2,6-dimethyl-benzonitrile, or a pharmaceutically acceptable salt thereof.

* * * * *